United States Patent
Morimoto et al.

(10) Patent No.: US 10,605,782 B2
(45) Date of Patent: Mar. 31, 2020

(54) WEDGE TAPPING DEVICE FOR ROTATING ELECTRICAL MACHINE, WEDGE INSPECTION SYSTEM FOR ROTATING ELECTRICAL MACHINE AND WEDGE TAPPING METHOD FOR ROTATING ELECTRICAL MACHINE

(71) Applicant: MITSUBISHI ELECTRIC CORPORATION, Chiyoda-ku (JP)

(72) Inventors: Yoshihiro Morimoto, Chiyoda-ku (JP); Daisuke Mizuno, Chiyoda-ku (JP); Kazuhiko Fukushima, Chiyoda-ku (JP); Kohei Nakamura, Chiyoda-ku (JP)

(73) Assignee: MITSUBISHI ELECTRIC CORPORATION, Chiyoda-ku (JP)

( * ) Notice: Subject to any disclaimer, the term of this patent is extended or adjusted under 35 U.S.C. 154(b) by 0 days.

(21) Appl. No.: 16/086,905

(22) PCT Filed: Jan. 23, 2017

(86) PCT No.: PCT/JP2017/002162
§ 371 (c)(1),
(2) Date: Sep. 20, 2018

(87) PCT Pub. No.: WO2017/175446
PCT Pub. Date: Oct. 12, 2017

(65) Prior Publication Data
US 2019/0101510 A1   Apr. 4, 2019

(30) Foreign Application Priority Data

Apr. 8, 2016   (JP) ................................. 2016-077740

(51) Int. Cl.
*G01N 29/12* (2006.01)
*G01N 29/24* (2006.01)
(Continued)

(52) U.S. Cl.
CPC .............. *G01N 29/12* (2013.01); *G01M 7/08* (2013.01); *G01N 29/045* (2013.01); *G01N 29/14* (2013.01);
(Continued)

(58) Field of Classification Search
CPC ........ G01N 29/12; G01N 29/24; G01N 29/22; G01N 29/04
See application file for complete search history.

(56) References Cited

U.S. PATENT DOCUMENTS

| 4,962,660 A | 10/1990 | Dailey et al. |
| 2009/0301168 A1 | 12/2009 | Moore |

FOREIGN PATENT DOCUMENTS

| JP | S51-093277 A | 8/1976 |
| JP | 2-241340 A | 9/1990 |

(Continued)

OTHER PUBLICATIONS

International Search Report dated Apr. 4, 2017 in PCT/JP2017/002162 filed Jan. 23, 2017.
(Continued)

*Primary Examiner* — David Z Huang
(74) *Attorney, Agent, or Firm* — Oblon, McClelland, Maier & Neustadt, L.L.P.

(57) ABSTRACT

A wedge tapping device for a rotating electrical machine to be inserted through a gap between a rotor and a stator to tap a wedge. The wedge tapping device includes: a tapping portion configured to tap the wedge and having a tapping force measuring portion configured to measure a tapping force of the tapping; an energy supplying portion configured to apply tapping energy to the tapping portion; an absorbing portion configured to suppress energy to be applied to the tapping portion; and a tapping arm, on which the tapping portion is disposed, and which has a longitudinal direction (Continued)

in a direction perpendicular to a direction in which the tapping portion performs tapping. The tapping arm is disposed so that the longitudinal direction is parallel to a rotation axis when the tapping is performed in the gap.

8 Claims, 14 Drawing Sheets

(51) Int. Cl.
    *G01N 29/22*     (2006.01)
    *G01N 29/14*     (2006.01)
    *G01N 29/04*     (2006.01)
    *G01M 7/08*     (2006.01)

(52) U.S. Cl.
    CPC ............. *G01N 29/22* (2013.01); *G01N 29/24* (2013.01); *G01N 2291/0258* (2013.01); *G01N 2291/2693* (2013.01)

(56) References Cited

FOREIGN PATENT DOCUMENTS

| | | |
|---|---|---|
| JP | 3-32339 A | 2/1991 |
| JP | 5-223697 A | 8/1993 |
| JP | 6-201533 A | 7/1994 |
| JP | 2003-254948 A | 9/2003 |
| JP | 2004-177136 A | 6/2004 |
| JP | 2012-112796 A | 6/2012 |

OTHER PUBLICATIONS

Notice of Reasons for Refusal issued in corresponding Japanese Application No. 2017-534752 dated Aug. 1, 2017 (with English translation).

Extended European Search Report issued in corresponding European Application No. 17778825.4 dated Oct. 25, 2019.

WEDGE TAPPING DEVICE FOR ROTATING ELECTRICAL MACHINE, WEDGE INSPECTION SYSTEM FOR ROTATING ELECTRICAL MACHINE AND WEDGE TAPPING METHOD FOR ROTATING ELECTRICAL MACHINE

TECHNICAL FIELD

The present invention relates to a wedge tapping device configured to tap a wedge in order to inspect wedge looseness without pulling out a rotor of a rotating electrical machine, and to a wedge inspection system using the device.

BACKGROUND ART

In the related art, there has been disclosed a wedge tapping device for a rotating electrical machine, which is configured to swing by a drive force from an air cylinder through intermediation of a link mechanism to instantly tap a wedge surface (for example, Patent Literature 1).

CITATION LIST

Patent Literature

[PTL 1] JP 02-241340 A

SUMMARY OF INVENTION

Technical Problem

It has been difficult to configure the related-art wedge tapping device for a rotating electrical machine, which includes a measuring instrument configured to measure a tapping input waveform, such that the wedge tapping device is insertable through a gap between a rotor and a stator to sufficiently tap a wedge of the rotating electrical machine. Specifically, depending on the rotating electrical machine to be inspected, there have been such problems that the device cannot enter the gap between the rotor and the stator, a sufficient tapping force cannot be obtained, and the tapping does not sufficiently reach the wedge.

The present invention has been made to solve the above-mentioned problems, and provides a wedge tapping device for a rotating electrical machine, which can be inserted through a gap between a rotor and a stator of a rotating electrical machine, can obtain a sufficient tapping force, and can measure tapping input.

Solution to Problem

According to one embodiment of the present invention, there is provided a wedge tapping device for a rotating electrical machine, which is to be inserted through a gap between a rotor and a stator of the rotating electrical machine to tap a wedge of the rotating electrical machine, the wedge tapping device including: a tapping portion, which is configured to tap the wedge of the rotating electrical machine, and includes a tapping force measuring instrument configured to measure a tapping force at the time of tapping; an energy supplying portion configured to apply tapping energy to the tapping portion; an absorbing portion configured to suppress energy to be applied to the tapping portion; and a tapping arm, on which the tapping portion is disposed, and which has a longitudinal direction in a direction perpendicular to a direction in which the tapping portion performs tapping, wherein the tapping arm is disposed so that the longitudinal direction is perpendicular to a circumferential direction of the rotor when the tapping is performed in the gap, and wherein the tapping portion, the energy supplying portion, and the absorbing portion are disposed in parallel along the longitudinal direction of the tapping arm.

Advantageous Effects of Invention

According to one embodiment of the present invention, there is obtained an effect in that, while the device has a form that can be inserted through the gap between the rotor and the stator of the rotating electrical machine, the tapping input waveform can be measured, and a sufficient tapping force can be obtained.

BRIEF DESCRIPTION OF DRAWINGS

FIGS. 10A and 10B are a view for illustrating the configuration of the wedge tapping device according to the second embodiment of the present invention.

DESCRIPTION OF EMBODIMENTS

First Embodiment

Figure 1A:
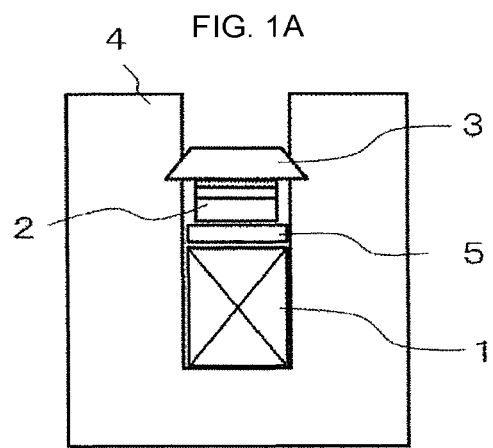
FIGS. 1A and 1B are a view for illustrating a structure of a stator of a rotating electrical machine.
Figure 1B:
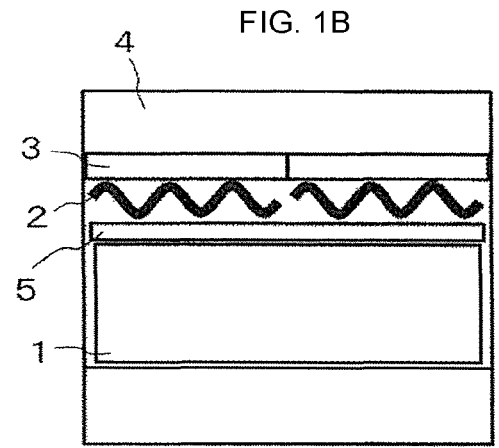
Figure 2:
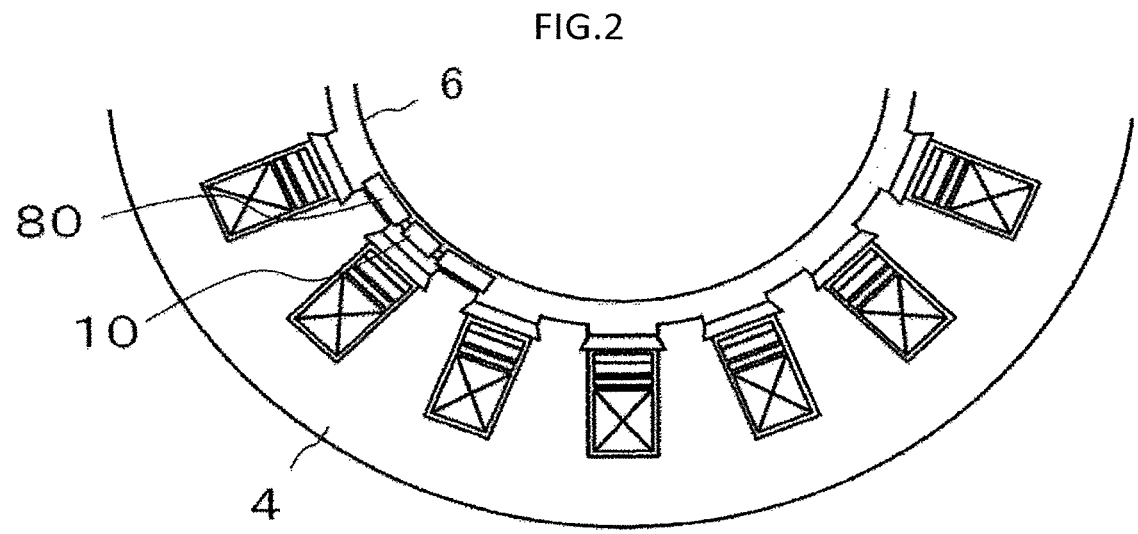
FIG. 2 is a conceptual view at a time when a wedge tapping-examination device is inserted between a rotor and the stator of the rotating electrical machine.

FIGS. 1A and 1B are a view for illustrating a structure of a stator of a rotating electrical machine that is an inspection target of the present invention. The rotating electrical machine includes a rotor 6 configured to rotate, and a stator 4 configured not to move with respect to the rotor 6. In FIGS. 1A and 1B, a coil 1 is retained so as to be pressed against the stator 4 by a wedge 3 disposed in an opening of a groove of the stator 4 through intermediation of a ripple spring 2. In this manner, the coil 1 is held inside the groove of the stator 4.

The strength of the force to retain the coil 1 by the ripple spring 2 at the time point at which the rotating electrical machine is manufactured is determined based on the amount of deflection of the ripple spring 2. Further, the strength of the force to retain the coil 1 is adjusted by the thickness of a shim 5 to be inserted.

The force to retain the coil 1 is reduced due to secular change of the rotating electrical machine, thermal stress at the time of activation, or other causes. The force to retain the coil 1 is reduced because an insulating layer of the coil 1 gradually deteriorates due to secular change or thermal stress, and a gap between the wedge 3 and the coil 1 is increased to loosen the wedge 3.

When the force to retain the coil 1 is reduced, the coil 1 vibrates due to its own electromagnetic force or mechanical vibration of the machine, and the insulating layer of the coil 1 rapidly wears. As a result, electrical insulation of the coil 1 cannot be sufficiently maintained, and the stator 4 and the coil 1 are short-circuited. Consequently, the rotating electrical machine may be stopped, damaged, or have an accident.

In order to prevent the above-mentioned problems in advance, a large-sized rotating electrical machine is periodically subjected to inspection of looseness of the wedge 3. When the looseness position is determined by the inspection, measures such as re-driving the wedge 3 are performed so that the coil 1 is always fixed with a sufficient retaining force.

In order to inspect the looseness of the wedge 3 as described above, the wedge 3 is tapped, and a tapping waveform and a vibration waveform are measured. Then, whether the wedge 3 is loose is inspected based on the tapping waveform and the vibration waveform. In this case, in order to perform the inspection without pulling out the rotor 6 of the rotating electrical machine, there is considered a device to be inserted through the gap between the rotor 6 and the stator 4 of the rotating electrical machine to measure the wedge tapping and vibration waveforms. In a first embodiment of the present invention, description is given of a wedge tapping device 10 configured to tap the wedge 3 during the inspection.

Figure 3:
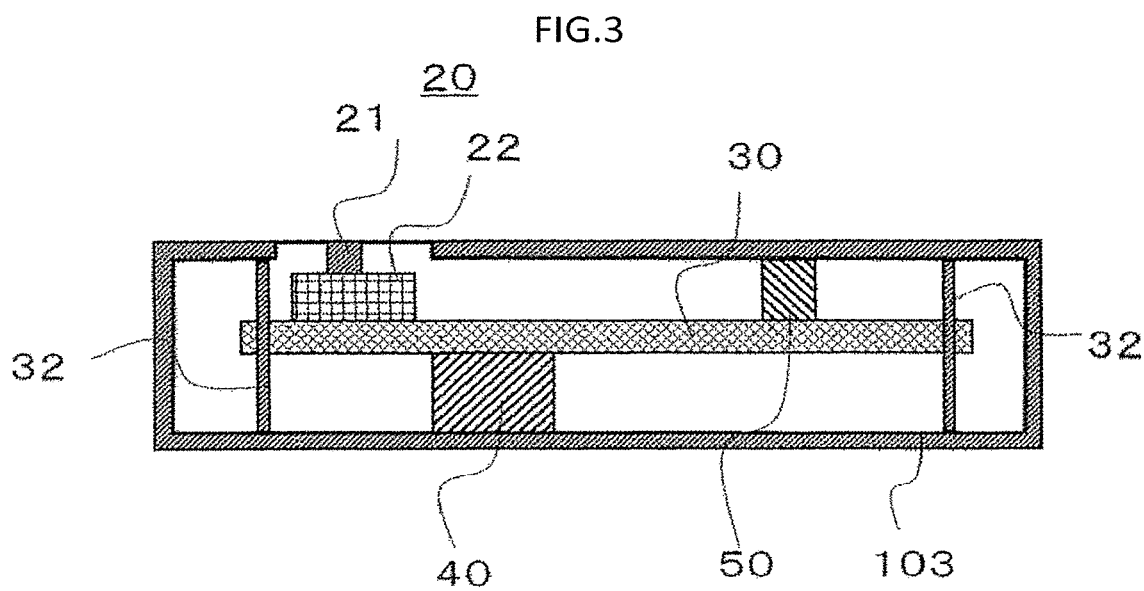
FIG. 3 is a sectional view for illustrating a configuration of a wedge tapping device according to a first embodiment of the present invention.

FIG. 3 is a conceptual view for illustrating a configuration of the wedge tapping device 10 for a rotating electrical machine according to the first embodiment of the present invention. In FIG. 1, the wedge tapping device 10 includes a tapping portion 20 configured to tap the wedge 3 of the rotating electrical machine, an energy supplying portion 40 configured to apply tapping energy to the tapping portion 20, an absorbing portion 50 configured to suppress the energy to be applied to the tapping portion 20, and a tapping arm 30, on which the tapping portion 20 is disposed, and which has a longitudinal direction in a direction perpendicular to the direction in which the tapping portion 20 performs tapping.

In this case, the tapping arm 30 is disposed so that its longitudinal direction is perpendicular to the direction in which the tapping portion performs tapping when the device examines the wedge 3 by tapping in the gap between the rotor 6 and the stator 4 of the rotating electrical machine. Further, the tapping portion 20, the energy supplying portion 40, and the absorbing portion 50 are in contact with the tapping arm 30, and are disposed in parallel along the longitudinal direction of the tapping arm 30. The tapping arm 30 is disposed so that its longitudinal direction is perpendicular to the direction in which the tapping portion performs tapping under a state in which the tapping arm 30 is parallel to a bottom surface of a casing 11.

Further, the tapping portion 20 includes a tapping force measuring instrument 22 configured to measure a tapping force at which the tapping portion 20 taps the wedge 3. It is preferred that the tapping force measuring instrument 22 be disposed on an extension line in a tapping direction of a point at which the tapping portion 20 is brought into contact with the wedge 3, and the tapping force measuring instrument 22 be fixed to the tapping arm 30. A tapping member 21 is disposed at the point at which the tapping portion 20 is brought into contact with the wedge 3.

As an energy source of the energy supplying portion 40, an electromagnetic force caused by use of an electromagnet, an elastic force of a spring or the like, or a combination thereof can be used. Specifically, the energy supplying portion 40 can be constructed of an actuator using an electromagnet, a spring, or a combination thereof.

The tapping arm 30 receives the energy that is stored in the energy supplying port ion 40 and released by the energy supplying portion 40 to operate so that the tapping portion 20 taps the wedge 3.

After the tapping portion 20 taps the wedge 3, the tapping arm 30 jumps back by a reaction force to move in a direction of returning to its original state. The absorbing portion 50 is configured to suppress and adjust the surplus energy of the tapping force to prevent the tapping arm 30 from receiving the force from the energy supplying portion 40 again to tap the wedge 3. More specifically, in the absorbing portion 50, the wedge 3 is displaced due to the impact of tapping the wedge 3 by the tapping arm 30. In this case, the absorbing portion 50 is configured to suppress the tapping force after the collision to prevent the tapping arm 30 from receiving the force from the energy supplying portion 40 again to tap the wedge 3. The surplus energy is a kinetic energy that the tapping arm 30 has after the first collision. In this case, it can be said that the absorbing portion 50 absorbs the surplus energy generated when the tapping portion 20 taps the wedge 3 (the same holds true also in the following embodiments).

For example, the absorbing portion 50 is constructed of an elastic body, for example, a spring or a shock absorbing member. With this configuration, the tapping portion 20 is prevented from tapping or being brought into contact with the wedge 3 two times or more, and the tapping force exhibits one waveform. Thus, the vibration output waveform can be properly determined.

Further, linear guides 32 configured to define the movement of the tapping arm 30 so as to move in the tapping direction may be provided.

As described above, when the wedge tapping device 10 according to the first embodiment examines the wedge 3 by tapping in the gap between the rotor 6 and the stator 4 of the rotating electrical machine, the longitudinal direction of the tapping arm 30 is oriented parallel to a rotation axis of the rotor 6. In this manner, the longitudinal direction of the entire wedge tapping device 10 also matches the longitudinal direction of the tapping arm 30, and thus the entire wedge tapping device 10 can easily enter the gap between the rotor 6 and the stator 4. The reason is as follows. Although a long object cannot be disposed in a circumferential direction in which the rotor 6 of the rotating electrical machine rotates, when the wedge tapping device 10 is inserted through the gap between the rotor 6 and the stator 4, the wedge tapping device 10 is longer in the rotation axis direction of the rotor 6 than in the circumferential direction of the rotating electrical machine, and thus the insertion is facilitated.

Further, as described above, in the wedge tapping device 10 according to the first embodiment, the tapping portion 20, the energy supplying portion 40, and the absorbing portion 50 are in contact with the tapping arm 30, and are disposed in parallel along the longitudinal direction of the tapping arm 30. With this configuration, the components of the wedge tapping device 10 do not overlap in a radial direction of the rotation in which the rotor 6 of the rotating electrical machine rotates, and there is provided such an effect that the radial length of the rotating electrical machine can be reduced. With this, the wedge tapping device 10 can be easily inserted through the gap between the rotor 6 and the stator 4.

Next, further specific configuration examples are described.

Figure 4A:
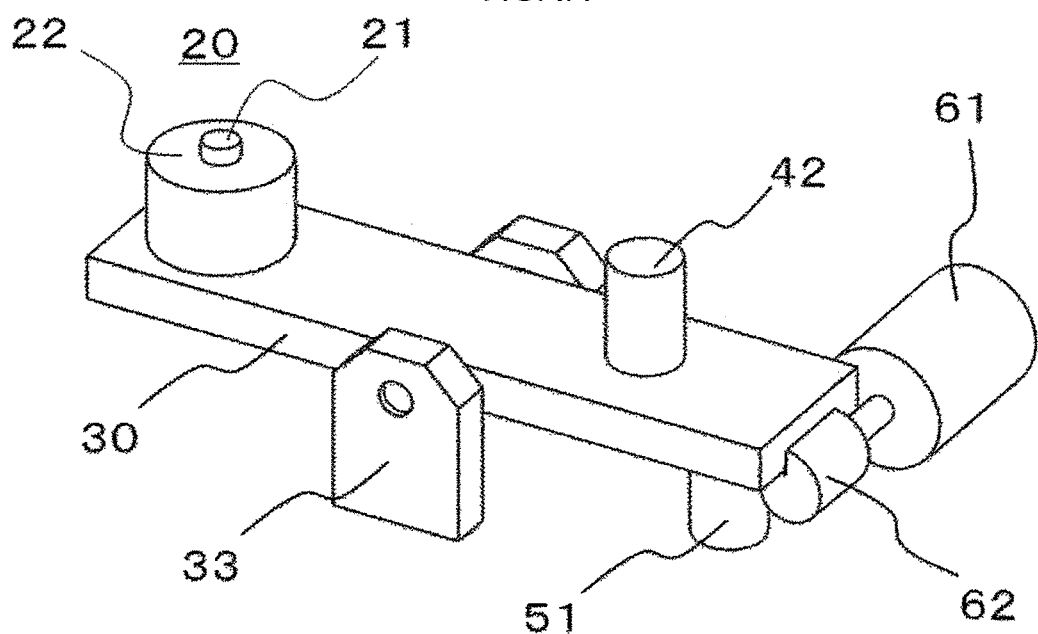
FIGS. 4A, 4B, and 4C are a view for illustrating the configuration of the wedge tapping device according to the first embodiment of the present invention.
Figure 4B:
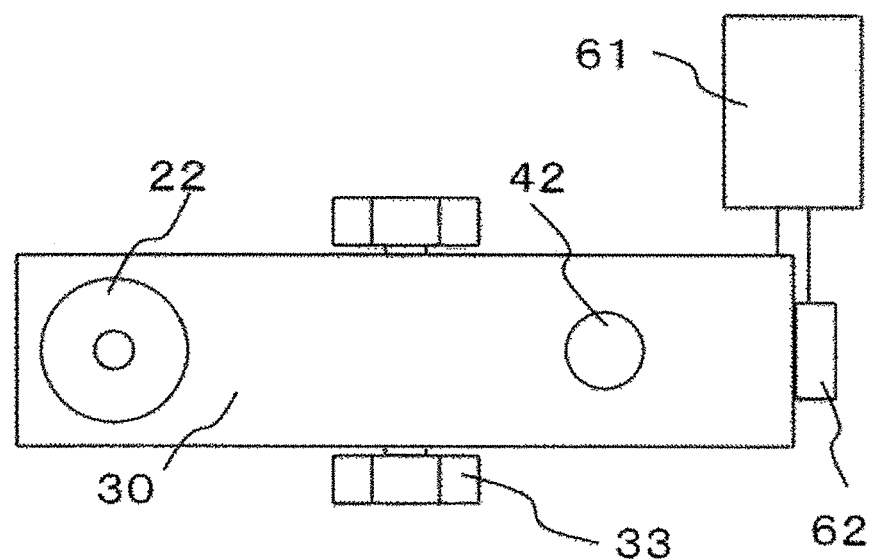
Figure 4C:
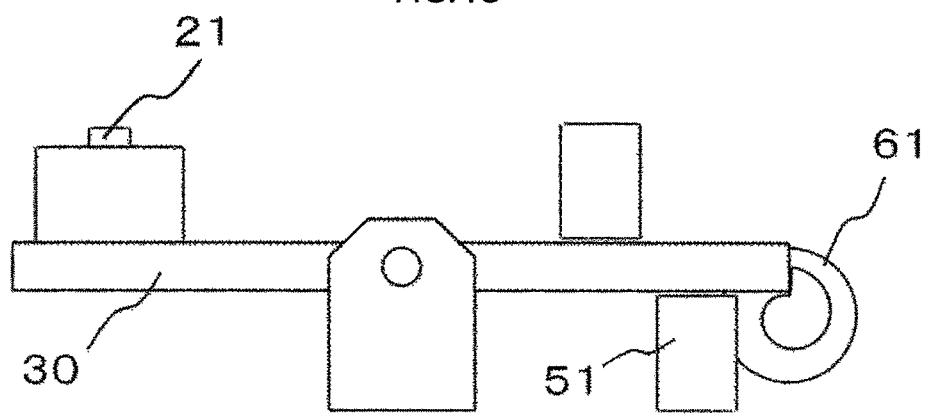

FIGS. 4A, 4B and 4C are a configuration view for illustrating the wedge tapping device 10 according to the first embodiment. In FIGS. 4A, 4B and 4C, the wedge tapping device 10 includes the tapping member 21 serving as a member configured to tap the wedge 3, the tapping force measuring instrument 22 connected to the tapping member 21, the tapping arm 30 having one end holding the tapping member 21 and the tapping force measuring instrument 22 (collectively referred to as tapping portion 20), a pivot support portion 33 fixed to a main body and configured to hold the tapping arm 30 so as to be pivotable (rotatable), a cam 62 held in contact with another end of the tapping arm 30, which is different from the end at which the tapping portion 20 is held, a motor 61 configured to rotate the cam 62, a tapping elastic body 42 serving as the energy supplying portion 40 configured to apply the tapping energy to the tapping portion 20, and a double-tapping preventing elastic body 51 serving as the absorbing portion 50 configured to suppress the energy to be applied to the tapping portion 20. In this case, the main body means the casing of the wedge tapping device 10.

In this case, the tapping arm 30 is disposed so that its longitudinal direction is parallel to the rotation axis of the rotor 6 when the wedge 3 is examined by tapping in the gap between the rotor 6 and the stator 4 of the rotating electrical machine. Further, the tapping portion 20, the energy supplying portion 40, and the absorbing portion 50 are in contact with the tapping arm 30, are disposed in parallel along the longitudinal direction of the tapping arm 30, and are mounted to the casing 11. In this case, the casing 11 is a casing of the wedge tapping device 10 for a rotating electrical machine. In this example, the tapping portion 20, the energy supplying portion 40, the fulcrum of the pivot support portion 33, the absorbing portion 50, the cam 62, and the motor 61 are disposed in the stated order along the longitudinal direction of the tapping arm 30. Further, the points at which the tapping arm 30 is in contact with the tapping portion 20, the energy supplying portion 40, the fulcrum of the pivot support portion 33, the absorbing portion 50, the cam 62, and the motor 61 are also disposed in the stated order along the longitudinal direction.

The tapping member 21 and the tapping force measuring instrument 22 construct the tapping portion 20. In the tapping portion 20, the tapping member 21 may be disposed on the tapping force measuring instrument 22. The tapping member 21 is disposed so that the tapping portion 20 is brought into local contact with the wedge 3, and is only required to be configured so that the tapping force is easily transferred to the tapping force measuring instrument 22.

The cam 62 is a plate cam having the tapping arm 30 as a follower member. A cam curve (cam profile) of the cam 62 gradually increases in height, and has a part in which the height sharply decreases. A contour shape of the cam 62 gradually increases in radius about a rotation axis, and has a part in which the radius sharply decreases. The cam 62 and the motor 61 control the energy of the tapping elastic body 42 serving as the energy supplying portion 40 from storage to release.

In this case, the cam 62 and the motor 61 are disposed so that their rotation axes are perpendicular to the longitudinal direction of the tapping arm 30, and also perpendicular to the tapping direction.

Therefore, the cam 62 is positioned so as to be in contact with the tapping arm 30 at least at any one position. Rotation of the motor 61 causes the cam 62 to gradually move the tapping arm 30 about the fulcrum of the pivot support portion 33 so that energy is stored in the tapping elastic body 42 serving as the energy supplying portion 40. After that, the tapping arm 30 suddenly becomes freely pivotable about the fulcrum of the pivot support portion 33 in a part of the cam curve that sharply decreases, and the energy stored in the tapping elastic body 42 is released to move the tapping arm 30 at once. This movement causes the tapping portion 20 held at the end of the tapping arm 30 to tap the wedge 3.

In FIGS. 4A, 4B and 4C, the tapping elastic body 42 serving as the energy supplying portion 40 is disposed on the opposite side of the tapping portion 20 across the fulcrum of the pivot support portion 33 in view of the positional relationship in the longitudinal direction of the tapping arm 30. Further, in view of the positional relationship in the tapping direction that is perpendicular to the longitudinal direction of the tapping arm 30, the tapping elastic body 42 is disposed on the same side as the tapping portion 20.

Further, the double-tapping preventing elastic body 51 serving as the absorbing portion 50 is disposed on the opposite side of the tapping portion 20 across the fulcrum of the pivot support portion 33 in view of the positional relationship in the longitudinal direction of the tapping arm 30. Further, in view of the positional relationship in the tapping direction that is perpendicular to the longitudinal direction of the tapping arm 30, the double-tapping preventing elastic body 51 is disposed on the opposite side of the tapping portion 20.

Figure 5A:
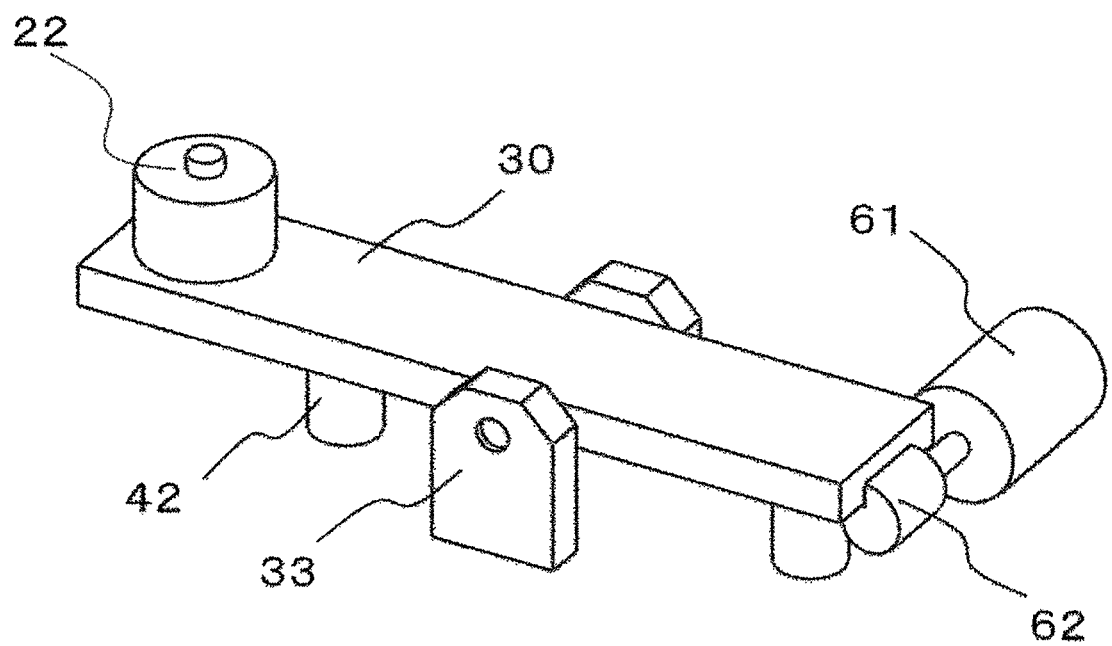
FIGS. 5A and 5B are a view for illustrating the configuration of the wedge tapping device according to the first embodiment of the present invention.
Figure 5B:
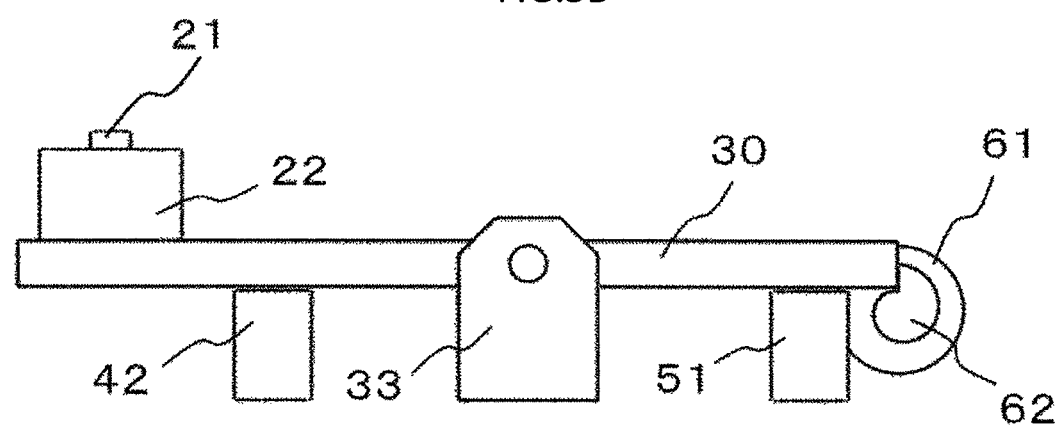

The tapping elastic body 42 and the double-tapping preventing elastic body 51 may be disposed as illustrated in FIGS. 5A and 5B other than the disposition of FIGS. 4A, 4B and 4C. In FIGS. 5A and 5B, the tapping elastic body 42 is disposed on the same side as the tapping portion 20 across the fulcrum of the pivot support portion 33 in view of the positional relationship in the longitudinal direction of the tapping arm 30. Further, in view of the positional relationship in the tapping direction that is perpendicular to the longitudinal direction of the tapping arm 30, the tapping elastic body 42 is disposed on the opposite side of the tapping portion 20. Further, the double-tapping preventing elastic body 51 is disposed at a position similar to that in FIGS. 4A, 4B and 4C.

As described above, in view of the positional relationship in the longitudinal direction of the tapping arm 30, the tapping elastic body 42 is disposed on the same side as the tapping portion 20 across the fulcrum of the pivot support portion 33, and the double-tapping preventing elastic body 51 is disposed on the opposite side thereof. In view of the positional relationship in the tapping direction that is perpendicular to the longitudinal direction of the tapping arm 30, the tapping elastic body 42 is disposed on the opposite side of the tapping portion 20, and the double-tapping preventing elastic body 51 is disposed on the opposite side of the tapping portion 20. With this configuration, the tapping elastic body 42 being an element configured to drive the tapping arm 30, including the motor 61, and the double-tapping preventing elastic body 51 can all be disposed on the same side in view of the positional relationship perpendicular to the longitudinal direction of the tapping arm 30 on the opposite side of the tapping portion 20. Therefore, a disposition that is effective to thin the device can be achieved. The tapping elastic body 42 and the double-tapping preventing elastic body 51 have the same spring displacement direction, which is the tapping direction. That is, the efficiency is high also in terms of energy supply and absorption.

The tapping elastic body 42 serving as the energy supplying portion 40 can be constructed of, for example, a spring. The free length of the spring is preferred to be set to such a length that the spring is just in contact with the tapping arm 30 or is slightly short when the tapping arm 30 is located at a position at which the tapping arm 30 is in contact with the part of the cam 62 in which the cam curve sharply decreases.

The double-tapping preventing elastic body 51 serving as the absorbing portion 50 can be constructed of, for example, a spring. The free length of the spring of the double-tapping preventing elastic body 51 is preferred to be set to such a length that the spring is already contracted to some extent by the tapping arm 30 when the tapping arm 30 is located at a position at which the tapping arm 30 is in contact with the part of the cam 62 in which the cam curve sharply decreases.

When the tapping arm 30 is in position before the tapping arm 30 is brought into contact with the wedge 3, the free length of the spring of the tapping elastic body 42 and the spring of the double-tapping preventing elastic body 51 are preferred to have a relationship of a preload state.

Next, an action of the wedge tapping device 10 is described. When the motor 61 rotates, the cam 62 fixed to a rotary shaft of the motor 61 rotates. The cam 62 has such a diameter that, as the cam 62 is rotated, a radius of a part in contact with the tapping arm 30 gradually increases. Then, the tapping arm 30 in contact with the cam 62 pivots about the fulcrum of the pivot support portion 33. The tapping elastic body 42 contracts as the tapping arm 30 gradually pivots to store elastic energy.

Further, as the motor 61 and the cam 62 are rotated and at a moment at which the part of the cam 62 in which the cam curve sharply changes is in contact with the tapping arm 30, the diameter of the cam 62 suddenly reduces. At this time, the force to press down the tapping elastic body 42 is eliminated, and the elastic energy stored in the tapping elastic body 42 is rapidly released. Then, the tapping elastic body 42 rapidly pushes out the tapping arm 30 in a direction opposite to the pivot direction exerted so far about the fulcrum of the pivot support portion 33, and thus the tapping portion 20 taps the wedge 3. This means that the cam 62 has a shape that enables the tapping arm 30 to rotate in accordance with the rotation of a rotation driving portion (motor 61), to thereby store energy in the energy supplying portion 40 (tapping elastic body 42) and primarily release the stored energy to rotate the tapping arm 30. Specifically, the cam 62 has such a diameter that a diameter of a part in contact with the tapping arm when the energy supplying portion 40 (tapping elastic body 42) releases the energy (right before the release) is larger than a diameter of a part in contact with the tapping arm when the energy supplying portion 40 (tapping elastic body 42) stores energy (at the time of start of storage).

At this time, the tapping arm 30 is brought into contact with the double-tapping preventing elastic body 51 serving as the absorbing portion 50 to contract the double-tapping preventing elastic body 51. Then, the double-tapping preventing elastic body 51 applies a force in a direction in which the tapping arm 30 returns to its original posture, and the tapping force measuring instrument 22 moves in a direction of separating from the wedge 3 to return to its original position.

Further, the above-mentioned operation can be repeated by rotating the cam 62 to cause the tapping arm 30 to pivot about the fulcrum of the pivot support portion 33. The above-mentioned operation is performed by rotating the motor 61, and hence the operation can be stopped by stopping the rotation of the motor 61, and the operation can be restarted when the rotation of the motor 61 is started at any time point. In particular, the wedge looseness inspection repeats the operation of tapping the wedge 3 for examination at one position and then moving the device in the rotation axis direction of the rotor 6 to tap the wedge 3 for examination at another position. Therefore, the rotation of the motor 61 is preferred to be stopped while the device is moved to another position after the wedge 3 is examined by tapping at one position.

Further, the posture of the tapping arm 30 at the time when the tapping portion 20 taps the wedge 3 may be a posture parallel to the casing 11, a posture that brings the tapping portion 20 closer to the wedge 3, or a posture that brings the tapping portion 20 farther from the wedge 3. The posture of the tapping arm 30 at the time when the wedge 3 is tapped is adjusted by the distance between the wedge tapping device 10 and the wedge 3 and the height of the tapping portion 20 from the tapping arm 30.

According to the wedge tapping device 10 for a rotating electrical machine of the first embodiment of the present invention, the tapping portion 20, the energy supplying portion 40, and the absorbing portion 50 are in contact with the tapping arm 30, and are disposed in parallel along the longitudinal direction of the tapping arm 30 and disposed so that the longitudinal direction of the tapping arm 30 is parallel to the rotation axis of the rotor 6. Thus, main components are disposed in a direction perpendicular to the tapping direction, and thus the thickness of the device in the tapping direction can be reduced. Further, the main components are disposed in parallel to the rotation axis of the rotor 6, and hence the dimension of the wedge tapping device 10 in the circumferential direction of the rotor 6 can be suppressed to be small.

Further, in the wedge tapping device 10 for a rotating electrical machine according to the first embodiment, the tapping arm 30 including the tapping portion 20 at its end is supported by the pivot support portion 33 to be pivotable about the fulcrum. Therefore, the tapping portion 20 and the component for supplying and controlling the tapping force can be largely displaced in a direction different from the tapping direction. Further, a component such as the linear guide 32 that leads to waste of space in the thickness direction can be eliminated. Thus, a simple structure is obtained with a small number of components, and the components required for tapping are prevented from being disposed in the thickness direction (tapping direction). In this manner, a device that is thinner than the related-art device can be obtained.

Further, in the wedge tapping device 10 for a rotating electrical machine according to the first embodiment, when the energy supplying portion 40, the absorbing portion 50, the cam 62, and the motor 61 are disposed on one-side surface of the tapping arm 30, the wasted space can be effectively utilized to thin the device.

Further, the wedge tapping device 10 for a rotating electrical machine according to the first embodiment has a combination of the motor 61, the cam 62, and the tapping elastic body 42, and hence a large force can be easily generated. Thus, higher looseness determination accuracy of the wedge 3 can be ensured, and a wide variety of rotating electrical machines can be inspected.

Further, in the wedge tapping device 10 for a rotating electrical machine according to the first embodiment, a distance from the tapping portion 20 to the fulcrum of the pivot support portion 33 is larger than a distance from the double-tapping preventing elastic body 51 to the fulcrum of the pivot support portion 33. Further, in the wedge tapping device 10, a distance from the tapping portion 20 to the fulcrum of the pivot support portion 33 is larger than a distance from the tapping elastic body 42 to the fulcrum of the pivot support portion 33. With this configuration, a tapping stroke of the tapping portion 20 can be increased. In this manner, even when the double-tapping preventing elastic body 51 applies the same pushing return amount (or pushing return angle) of the tapping arm 30, the tapping portion 20 is more separated from the wedge 3, and hence an effect of suppressing double tapping is enhanced.

Further, the tapping stroke of the tapping portion 20 can be increased, and hence the acceleration distance by the tapping elastic body 42 obtained when the tapping portion 20 performs tapping can be increased. Therefore, there is provided such an effect that the tapping force can be increased without increasing the thickness of the device in the tapping direction. Further, even when the distance between the tapping elastic body 42 and the pivot support portion 33 is increased, the contraction amount of the tapping elastic body 42 can be increased to ensure a large elastic force. In this manner, when the distance between the tapping elastic body 42 and the pivot support portion 33 is increased, there is provided such an effect that the tapping force can be increased without increasing the thickness of the device in the tapping direction. For example, the distance between the tapping elastic body 42 and the pivot support portion 33 is preferred to be larger than the distance from the double-tapping preventing elastic body 51 to the fulcrum of the pivot support portion 33.

Second Embodiment

Figure 6A:
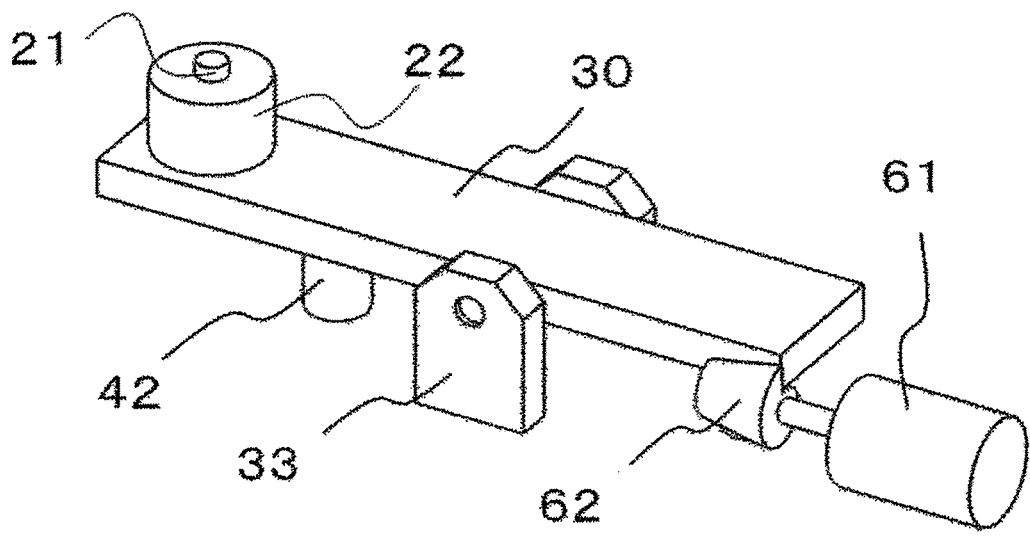
FIGS. 6A, 6B and 6C are a view for illustrating a configuration of a wedge tapping device according to a second embodiment of the present invention.
Figure 6B:
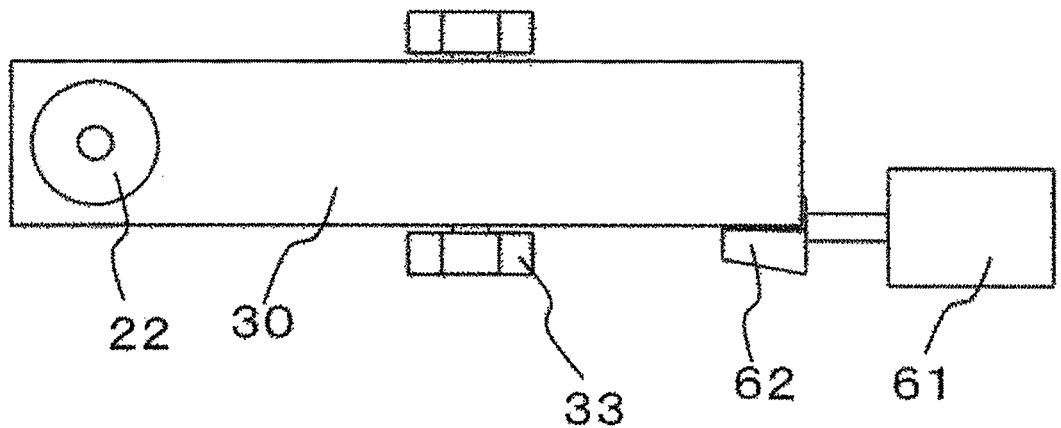
Figure 6C:
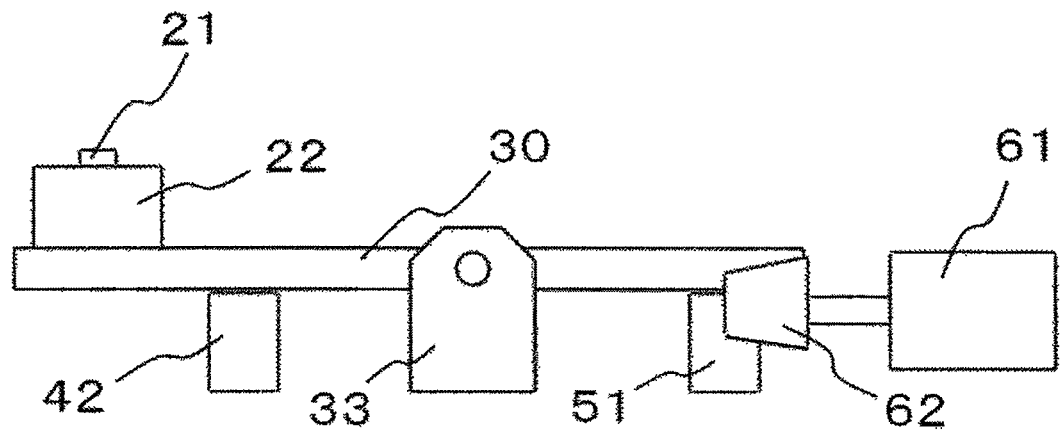

FIGS. 6A, 6B and 6C are a configuration diagram for illustrating a wedge tapping device 10 for a rotating electrical machine according to a second embodiment of the present invention. The second embodiment differs from the above-mentioned embodiment in the positional relationship between the pivot axis of the tapping arm 30 and the rotation axes of the cam 62 and the motor 61, and those axes have a perpendicular relationship. The same reference symbols as those in the above-mentioned embodiment denote the same components unless particularly noted.

In FIGS. 6A, 6B and 6C, the wedge tapping device 10 includes the tapping portion 20 configured to tap the wedge 3 of the rotating electrical machine, the energy supplying portion 40 configured to apply tapping energy to the tapping portion 20, the absorbing portion 50 configured to absorb surplus energy generated when the tapping portion 20 taps the wedge 3, and the tapping arm 30, on which the tapping portion 20 is disposed, and which has a longitudinal direction in a direction perpendicular to the direction in which the tapping portion 20 performs tapping. In this case, the absorbing portion 50 suppresses energy to be applied to the tapping portion 20. Further, the energy supplying portion 40 may be the tapping elastic body 42.

Further, the tapping arm 30 has the longitudinal direction in the direction perpendicular to the direction in which the tapping portion 20 performs tapping. The tapping arm 30 is disposed so that its longitudinal direction is perpendicular to the circumferential direction of the rotor 6 when tapping is performed in the gap between the rotor 6 and the stator 4 of the rotating electrical machine. The tapping portion 20, the energy supplying portion 40, and the absorbing portion 50 are disposed in parallel along the longitudinal direction of the tapping arm 30. Further, the points at which the tapping arm 30 is in contact with the tapping portion 20, the energy supplying portion 40, and the absorbing portion 50 may be located on one straight line in the longitudinal direction of the tapping arm 30. In this case, less torsion force is applied to the tapping arm 30, and there is provided such an effect that the tapping arm 30 can be thinned.

Further, the wedge tapping device 10 includes the tapping portion 20 at the end of the tapping arm 30. Further, the wedge tapping device 10 includes the pivot support portion 33 disposed on the casing 11 of the wedge tapping device 10 and configured to support the tapping arm 30 so as to be pivotable. Further, the distance between the fulcrum of the pivot support portion 33 and the tapping portion 20 is larger than the distance between the fulcrum of the pivot support portion 33 and the energy supplying portion 40 and the distance between the fulcrum and the absorbing portion 50.

Further, the wedge tapping device 10 includes the cam 62 configured to cause the tapping arm 30 to pivot about the fulcrum of the pivot support portion 33, and the rotation driving portion (motor 61) configured to rotate the cam 62. In this case, the rotation axis of the rotation driving portion (motor 61) is oriented perpendicular to the pivot axis of the tapping arm 30.

In FIGS. 6A, 6B and 6C, the motor 61 and the cam 62 are disposed at another end on the opposite side of the tapping portion 20 disposed at one end in view of the positional relationship in the longitudinal direction of the tapping arm 30. The rotation axes of the motor 61 and the cam 62 are oriented perpendicular to the pivot axis of the tapping arm 30. In FIGS. 6A, 6B and 6C, under a state in which no energy is stored in the tapping elastic body 42, the longitudinal direction of the tapping arm 30 is oriented parallel to the rotation axes of the motor 61 and the cam 62. Further, the rotation axes of the motor 61 and the cam 62 are positioned on the opposite side in the tapping direction of the tapping arm 30 in the state in which no energy is stored in the tapping elastic body 42.

Further, the cam 62 is not a simple plate cam whose diameter changes, but the diameter of the cam 62 also changes in the direction of the rotation axis. Specifically, the cam 62 has a cone or truncated cone shape when locally viewed at a position at which the tapping arm 30 is in contact with the cam 62. Such change in diameter is set at the same ratio for one revolution of the cam 62 with the maximum value being an upward pushing amount of the tapping arm 30 that depends on the distance from the pivot support portion 33, which is required for achieving the maximum inclination of the tapping arm 30.

In order to describe the shape of the cam 62, first, it is assumed that the cam 62 is rotated by one revolution in synchronization with the tapping arm 30 moving smoothly in an operation range from the posture of the tapping arm 30 at the time of tapping to the posture of the tapping arm 30 right before the tapping with the energy supplying portion 40 storing the maximum energy. Further, the shape of the cam 62 is determined so as to follow the position and the shape of the tapping arm 30 so that, at each rotational position, the tapping arm 30 and the cam 62 are in linear contact with each other.

Figure 7A:
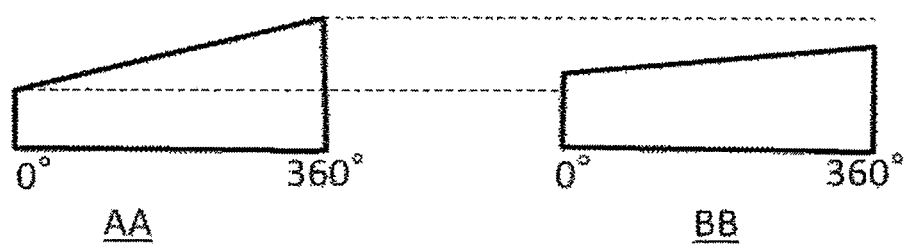
FIGS. 7A and 7B are views for illustrating a shape of a cam in the second embodiment of the present invention.
Figure 7B:
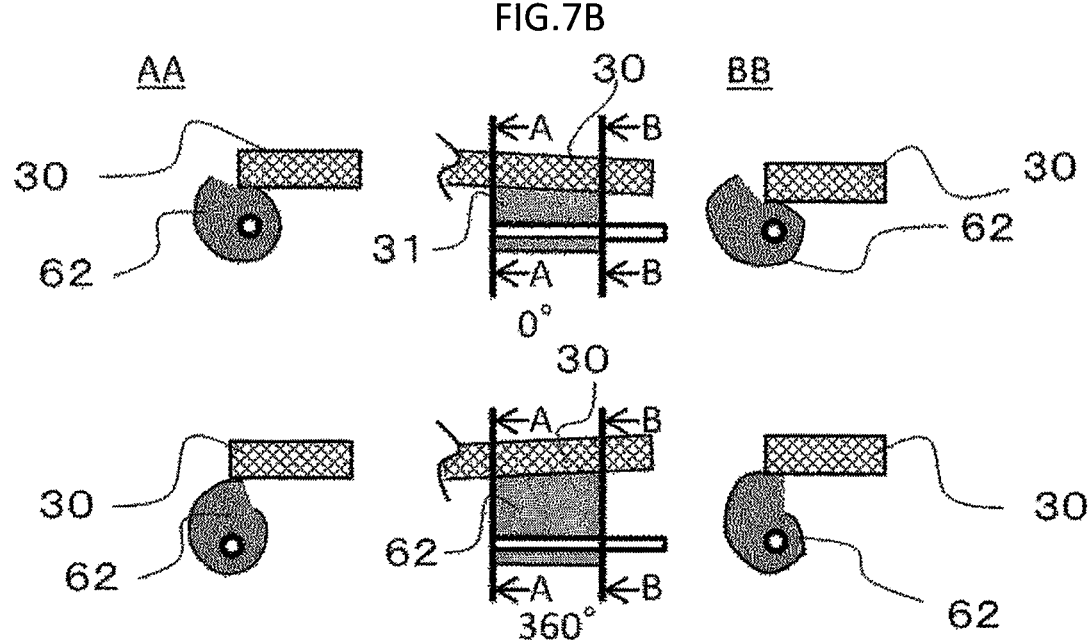

FIGS. 7A and 7B are illustrations of examples of the shape of the cam 62. FIG. 7A is an illustration of a cam profile, and FIG. 7B is a sectional view that is perpendicular to the rotation axis of the cam 62 and a sectional view that is parallel to the rotation axis of the cam 62 and perpendicular to the pivot axis of the pivot support portion 33. In both of FIG. 7A and FIG. 7B, a left side (AA) represents a cross-section of the cam 62 closer to the fulcrum of the pivot support portion 33, and a right side (BB) represents a cross-section farther therefrom. The center row of FIG. 7B is a sectional view that is parallel to the rotation axis of the cam 62 and perpendicular to the pivot axis of the pivot support portion 33.

FIG. 7(*a*) represents the cam profile of the cam 62. In FIG. 7(*a*), 0° represents a cam position corresponding to the posture at the time when the tapping arm 30 performs tapping, and 360° represents a cam position corresponding to the posture of the tapping arm 30 at the time right before the tapping with the energy supplying portion 40 storing the maximum energy. The cam 62 rotates so that its profile at a portion in contact with the tapping arm 30 changes from 0° to 360°, and returns to 0° after one revolution. In this case, the maximum cam profile is obtained at the time of 360°, and the minimum cam profile is obtained at the time of 0°. The energy supplying portion 40 stores the maximum energy when the cam 62 has the cam profile of 360°. When the cam 62 further rotates to have the cam profile of 0°, the retaining of the tapping arm 30 is released, and the energy stored in the energy supplying portion 40 is transmitted to the tapping arm 30 to achieve a tapping force of the tapping portion 20 as a result. Originally, 0° and 360° represent the same position. In this case, the rotation to 360° and then further to 0° represents the sharp decrease of the profile. This means that the cam 62 has a shape that enables the tapping arm 30 to rotate in accordance with the rotation of the rotation driving portion (motor 61), to thereby store energy in the energy supplying portion 40 (tapping elastic body 42) and primarily release the stored energy to rotate the tapping arm 30. The cam 62 has such a diameter that a diameter of a part in contact with the tapping arm when the energy supplying portion 40 (tapping elastic body 42) releases the energy (right before the release) is larger than a diameter of a part in contact with the tapping arm when the energy supplying portion 40 (tapping elastic body 42) stores energy (at the time of start of storage).

The cam 62 in the above-mentioned embodiment has a similar cam profile with the plate cam, but the cam 62 in the second embodiment has a feature in that a side of the cam 62 closer to the fulcrum of the pivot support portion 33 and a side of the cam 62 farther therefrom have different cam profiles. This is because the shape of the cam 62 is determined so as to follow the position and the shape of the tapping arm 30 so that, at each rotational position, the tapping arm 30 and the cam 62 are in linear contact with each other at the time of contact.

First, the profile of the cam 62 at the time of the position of 360° is considered. At this time, the energy supplying portion 40 stores the maximum energy, and hence the tapping arm 30 is in such a posture that the cam 62 side (or the side opposite to the tapping portion 20) from the fulcrum of the pivot support portion 33 is moved in the tapping direction so that the energy supplying portion 40 is contracted. This posture corresponds to the posture of the tapping arm 30 right before the tapping.

At this time, the tapping arm 30 is in such a posture that a distance from the rotation axis of the cam 62 is increased as a distance from the fulcrum of the pivot support portion 33 is increased. The cam profile of the cam 62 follows this posture, and the cam profile farther from the fulcrum of the pivot support portion 33 is larger than the cam profile closer thereto.

The profile of the cam 62 at the time when the cam 62 is rotated to be at a position of 0° is considered. At this time, the energy supplying portion 40 extends, and the tapping arm 30 pivots at the maximum in the tapping direction. The tapping arm 30 at this time has such a posture that the tapping portion 20 is moved at the maximum in the tapping direction, and in contrast, the cam 62 side (or the side opposite to the tapping portion 20) from the fulcrum of the pivot support portion 33 pivots so as to move to the side opposite to the tapping direction. This posture corresponds to the posture of the tapping arm 30 at the time of tapping.

At this time, the tapping arm 30 is in such a posture that the distance from the rotation axis of the cam 62 is increased as the distance from the fulcrum of the pivot support portion 33 is decreased. The cam profile of the cam 62 follows this posture, and the cam profile closer to the fulcrum of the pivot support portion 33 is larger than the cam profile farther therefrom.

The cam profile of the cam 62 increases smoothly from 0° to 360°. As described above, at the time of 0°, the cam profile closer to the fulcrum of the pivot support portion 33 is larger than the cam profile farther therefrom, and at the time of 360°, conversely, the cam profile farther from the fulcrum of the pivot support portion 33 is larger than the cam profile closer thereto.

In the above, description has been given of the sides of the cam 62 closer to and farther from the fulcrum of the pivot support portion 33. A part between the sides of the cam 62 closer to and farther from the fulcrum of the pivot support portion 33 basically has a shape obtained by connecting the sides with a straight line. This is because a part of the tapping arm 30 with which the cam 62 is brought into contact is flat.

When this part is curved, a contact line shape corresponding thereto is obtained.

FIG. 7(*b*) is an illustration representing the shape of the cam 62 having the above-mentioned cam profile in sectional view. In FIG. 7(*b*), the upper part represents a cam profile of 0° (at the time of tapping), and the lower part represents 360° (right before the tapping). An AA cross-section on the left side represents the side of the cam 62 closer to the fulcrum of the pivot support portion 33, and a BB cross-section on the right side represents the side of the cam 62 farther from the fulcrum of the pivot support portion 33.

As illustrated in FIG. 7(*b*), at the time of tapping (0°), the side of the tapping arm 30 farther from the tapping portion 20 pivots so as to move in a direction opposite to the tapping, and the tapping arm 30 extends downward to the right in FIG. 7(*b*). Further, right before the tapping (360°), the side of the tapping arm 30 farther from the tapping portion 20 pivots so as to move in the tapping direction, and the tapping arm 30 extends upward to the right in FIG. 7(*b*).

In the above, description has been given of the tapping arm 30 always being in contact with the cam 62, but the tapping arm 30 is not always required to be in contact with the cam 62. In actuality, after the tapping of the tapping arm 30, the surplus energy of the tapping is also absorbed by the absorbing portion 50. That is, the kinetic energy of the tapping arm 30 is absorbed by the absorbing portion configured to suppress the energy to be applied to the tapping portion 20. Therefore, after the tapping (0°), the tapping elastic body 42 is in a state of not storing energy, and the posture of the tapping arm 30 is determined depending on the relationship with the tapping elastic body 42 and the double-tapping preventing elastic body 51 with which the tapping arm 30 may be brought into contact. For example, when the natural lengths of the tapping elastic body 42 and the double-tapping preventing elastic body 51 are set to a length that brings the horizontal tapping arm 30 into contact with the elastic bodies, the tapping arm 30 is maintained horizontal until the cam 62 is brought into contact.

Therefore, in the cam profile of FIG. 7(*a*), a cam profile having a height equal to larger than a height of a profile at which the horizontal tapping arm 30 is in contact may be used, and, otherwise, the height may be substantially zero.

According to the wedge tapping device 10 for a rotating electrical machine of the second embodiment, the motor 61 and the cam 62 are configured so that their rotation axes are oriented in a direction perpendicular to the pivot axis of the tapping arm 30. Therefore, the motor 61, which is longer in the rotation axis direction than in the radial direction, can be disposed to be aligned in the longitudinal direction of the tapping arm 30, and thus there is provided such an effect that the length in the circumferential direction in which the rotating electrical machine rotates can be reduced. The wedge tapping device 10 according to the second embodiment can achieve a sufficient tapping force, and can be easily inserted through the gap between the rotor 6 and the stator 4 of the rotating electrical machine having a structure that is similarly longer in the axial direction.

According to the wedge tapping device 10 for a rotating electrical machine of the second embodiment, the upward pushing amount for achieving the maximum inclination of the tapping arm 30 is determined based on the distance of the cam 62 from the pivot support portion 33 of the tapping arm 30. With this upward pushing amount being set as the maximum value, the diameter of the cam 62 is changed at the same ratio for one revolution of the cam 62. Therefore, the cam 62 and the tapping arm 30 are in linear contact with each other, and thus the force can be reliably transmitted even when the tapping elastic body 42 is a strong spring.

Further, even when a large force is applied between the cam 62 and the tapping arm 30, the cam 62 and the tapping arm 30 are in linear contact with each other, and hence the wear is smaller as compared to the case of point contact. Therefore, a contact portion between the cam 62 and the tapping arm 30 is reduced in deterioration due to wear. Accordingly, there is provided such an effect that an accurate and appropriate tapping force can be exerted for a long period of time.

Further, the cam 62 of FIG. 7 is shaped so that the amount of change in diameter of the side farther from the fulcrum of the pivot support portion 33 is larger than the amount of change in diameter of the side closer to the fulcrum of the pivot support portion 33 of the cam 62. The reason is as follows.

First, when the tapping arm 30 pivots about the fulcrum of the pivot support portion 33, as a matter of course, the movement range of the side farther from the fulcrum of the pivot support portion 33 is larger than the movement range of the side closer to the fulcrum from the point. Further, the cam 62 is set so that the tapping arm 30 exerts a tapping motion when the cam 62 is rotated. That is, the cam 62 is shaped so as to follow the motion of the tapping arm 30 and is brought into linear contact with the tapping arm 30. In order to achieve this state, the amount of change in diameter of the cam 62 is also required to fall within the movement range of the tapping arm 30. Therefore, the amount of change in diameter of the cam 62 is required to be set so that the amount of change in diameter of the cam 62 on the side farther from the fulcrum is larger than the amount of change in diameter of the cam 62 on the side closer to the fulcrum so as to fall within the movement range of the tapping arm 30.

The above-mentioned amount of change in diameter of the cam 62 may be considered as an amount of change during which the energy stored in the tapping elastic body 42 changes from 0 to the maximum. In other words, the amount of change in diameter of the cam 62 is an amount of change from a diameter at a position of the cam 62 in contact with the tapping arm 30 at the time of tapping to a diameter at a position of the cam 62 in contact with the tapping arm 30 right before the next tapping. Further, the amount of change in diameter of the cam 62 may be considered as an amount of change per unit angle.

Figure 8A:
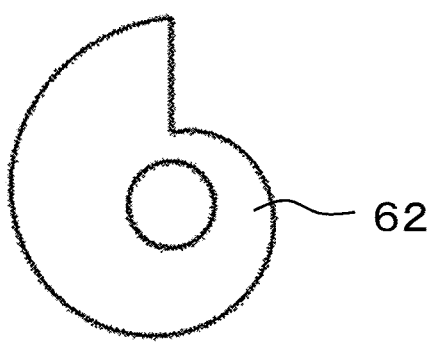
FIGS. 8A, 8B, 8C and 8D are views for illustrating the shape of the cam in the second embodiment of the present invention.
Figure 8B:
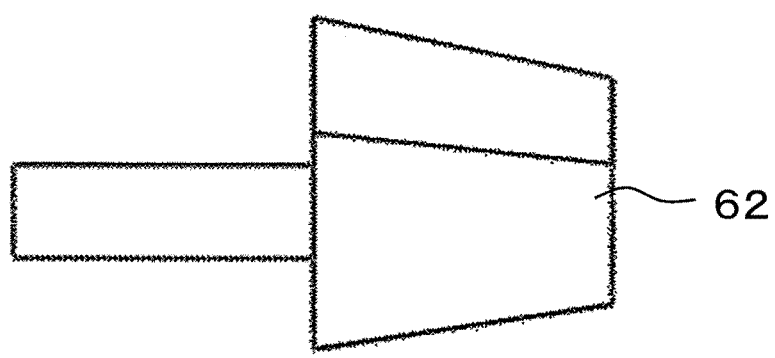
Figure 8C:
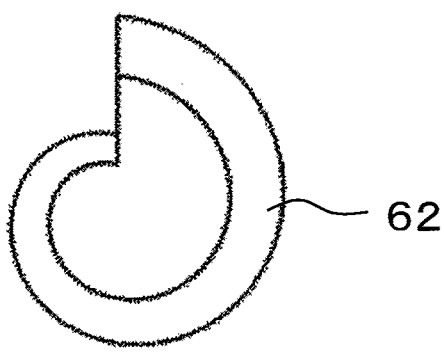
Figure 8D:
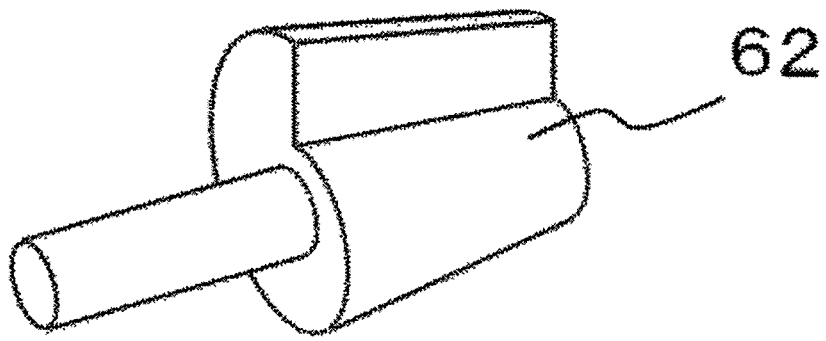

Further, FIGS. 8A, 8B, 8C and 8D are illustrations of a different shape of the cam 62. FIG. 8A is a side view of the cam 62 as viewed from the motor 61 side, FIG. 8B is a front view of the cam 62, FIG. 8C is a side view of the cam 62 as viewed from the pivot support portion 33 side, and FIG. 8D is a perspective view of the cam 62. In FIGS. 8A, 8B, 8C and 8D right after the tapping portion 20 performs tapping (the above-mentioned cam profile of 0°), the diameter of the cam 62 is larger on the motor 61 side than on the pivot support portion 33 side. When the cam 62 of FIGS. 8A, 8B, 8C and 8D is used, the tapping arm 30 at the time of tapping has such a posture that the end at which the tapping portion 20 is present is closer to the tapping elastic body 42 side with respect to the horizon. In order for the tapping portion 20 to tap the wedge 3 under this state, the height of the tapping portion 20 in the tapping direction is increased so that the tapping portion 20 (tapping member 21) can tap the wedge 3.

Figure 9A:
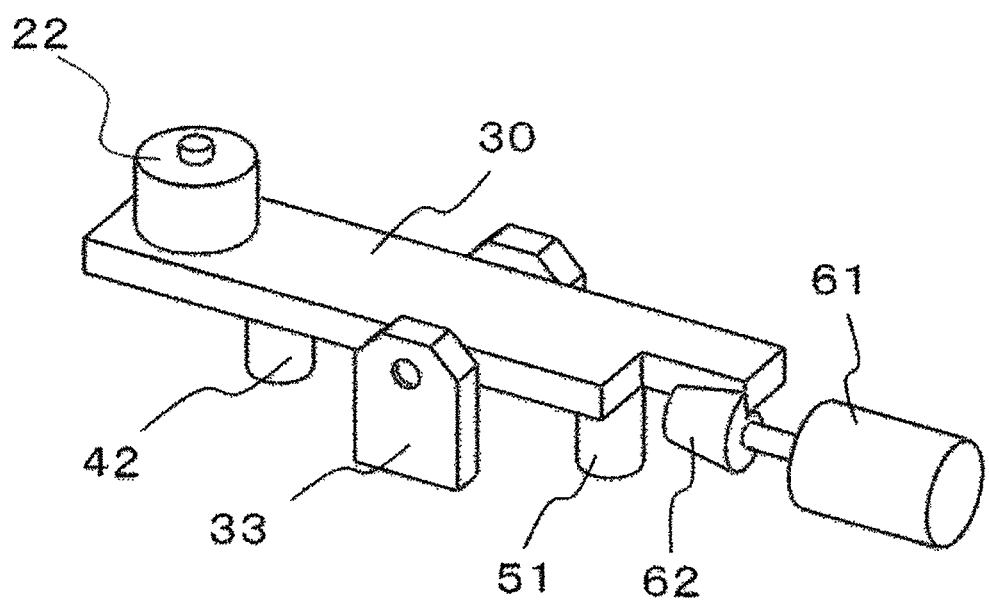
FIGS. 9A and 9B are a view for illustrating the configuration of the wedge tapping device according to the second embodiment of the present invention.
Figure 9B:
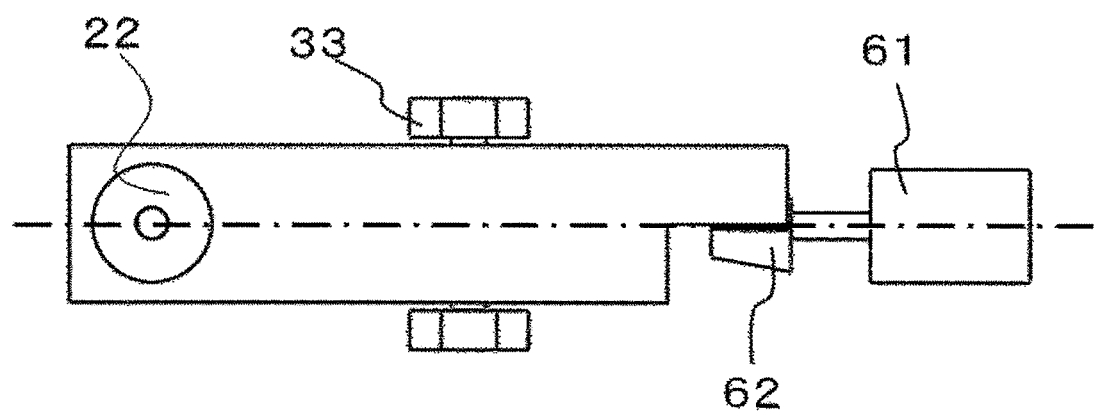

FIGS. 9A and 9B are a configuration view for illustrating another wedge tapping device 10 according to the second embodiment. In FIGS. 9A and 9B, the configuration differs from that in the example of FIGS. 6A, 6B and 6C in the positional relationship between the tapping arm 30 and the rotation axes of the motor 61 and the cam 62, and also in the shape of the end of the tapping arm 30.

In FIGS. 9A and 9B, the rotation axis of the cam 62 is disposed on the center line in the pivot axis direction of the tapping arm 30 (parallel to the longitudinal direction) when the wedge tapping device 10 is viewed from the tapping direction. In this case, the end of the tapping arm 30 on the side opposite to the side on which the tapping portion 20 is present is cut out to dispose the cam 62 and the motor 61 on the above-mentioned center line. When the wedge tapping device 10 is viewed from the tapping direction, the tapping member 21, the energy supplying portion 40, the absorbing portion 50, and the cam 62 are disposed on the center line of the tapping arm 30. With this, there is provided such an effect that, when the cam 62 is rotated to cause the tapping arm 30 to pivot, a torsion force is prevented from being applied to the tapping arm. This leads to such an effect that the tapping arm 30 can be thinned, and hence the wedge tapping device 10 can be further thinned.

Figure 10B:
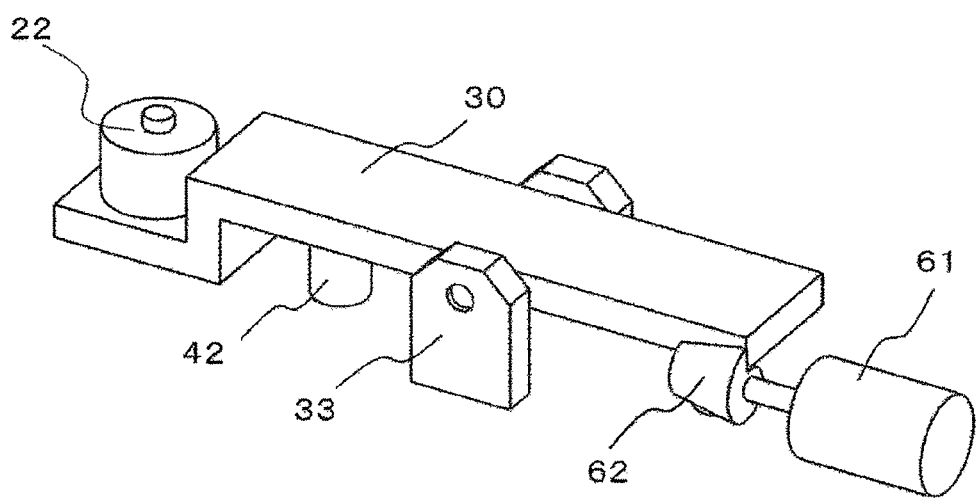
Figure 10B:
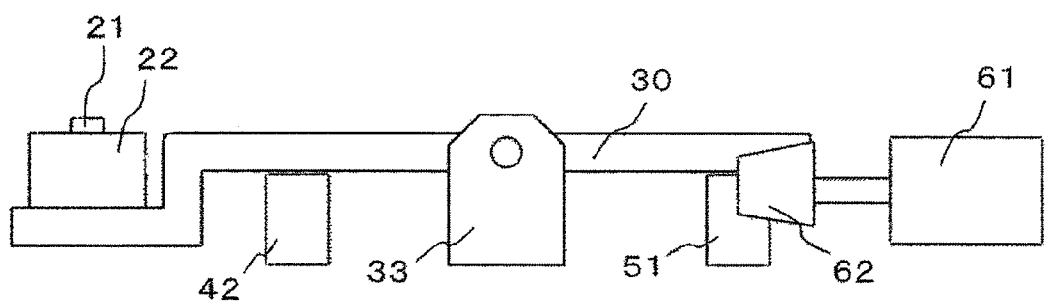

FIGS. 10A and 10B are a configuration view for illustrating another wedge tapping device 10 according to the second embodiment. In FIGS. 10A and 10B, the following points differ from those described above, but other configurations are similar to those described above.

In FIGS. 10A and 10B, the tapping arm 30 has an elbow-shaped structure having a recessed portion in a direction opposite to the tapping direction when the tapping arm 30 is viewed in the pivot axis direction of the tapping arm 30. The tapping portion 20 (tapping force measuring instrument 22) is disposed in the recessed portion. The depth of the recessed portion is set so that the tapping member 21 on the tapping force measuring instrument 22 is substantially flush with the upper surface of the pivot support portion 33 or is protruded by a required length from the upper surface of the pivot support portion 33.

According to the wedge tapping device 10 for a rotating electrical machine of the second embodiment, the protrusion amount of the tapping force measuring instrument 22 in the height direction can be suppressed to obtain a thin structure. Therefore, there can be obtained a structure that can be more easily applied to the rotating electrical machine having a narrow gap between the rotor 6 and the stator 4 while a sufficient tapping force is achieved. Further, the tapping arm 30 and the cam 62 are in linear contact with each other. Therefore, the linear contact between the cam 62 and the tapping arm 30 enables a stable operation, and a predetermined operation can be prevented from being changed due to wear.

Third Embodiment

Hitherto, it has been difficult to inspect rotating electrical machines having different gaps between the rotor 6 and the stator 4 or different intervals between the surface of the stator 4 and the wedge 3 with the same wedge tapping device 10. In a third embodiment of the present invention, description is given of a wedge tapping device 10 capable of inspecting the rotating electrical machines having different gaps between the rotor 6 and the stator 4 or different intervals between the surface of the stator 4 and the wedge 3.

Figure 11A:
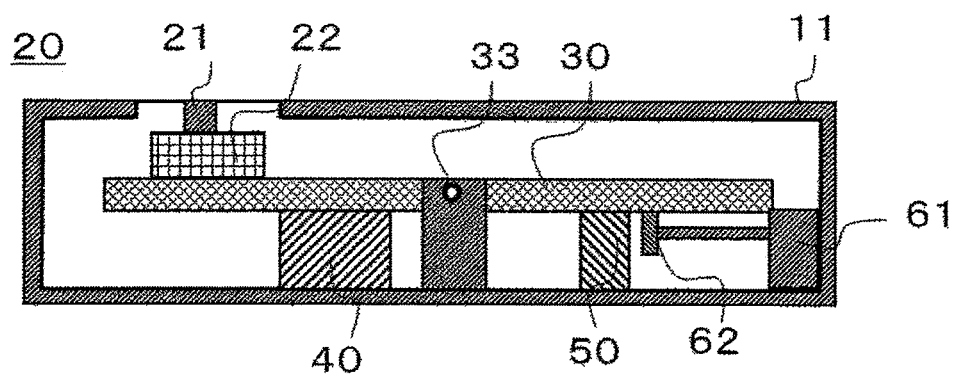
FIGS. 11A, 11B and 11C are sectional views for illustrating an operation of a wedge tapping device according to a third embodiment of the present invention.
Figure 11B:
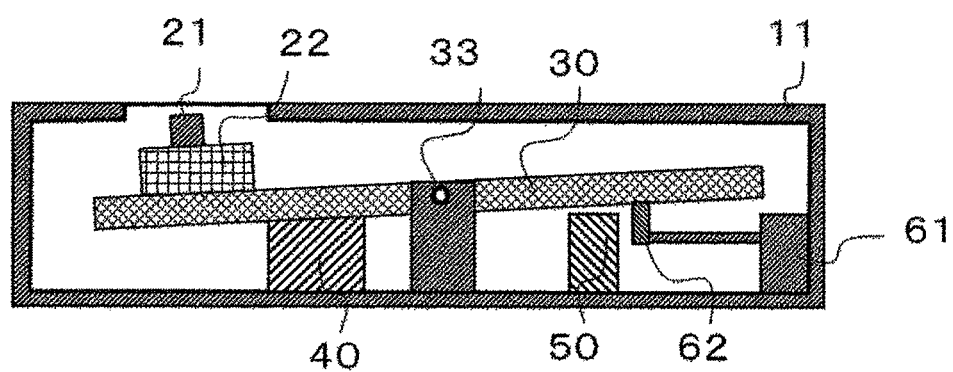
Figure 11C:
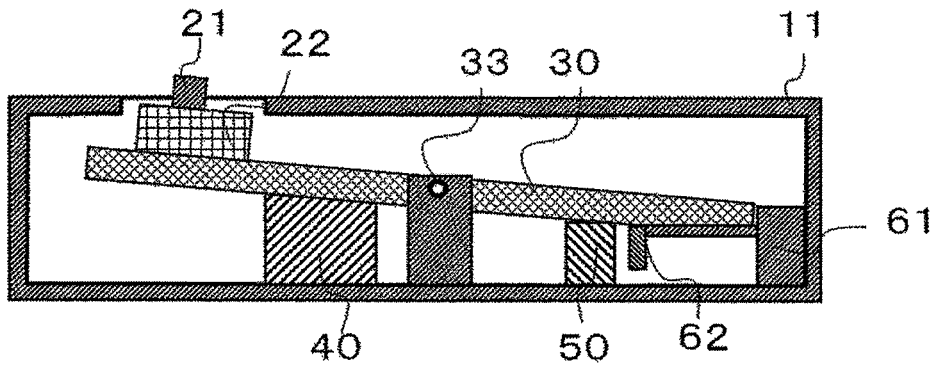

FIGS. 11A, 11B and 11C are sectional views for illustrating the configuration and the operation of the wedge tapping device 10 according to the third embodiment. FIG. 11A is an illustration of a configuration set to have a tapping force and a tapping stroke appropriate for the gap between the rotor 6 and the stator 4 or the interval between the surface of the stator 4 and the wedge 3 of a particular rotating electrical machine. In FIGS. 11A, 11B and 11C, components denoted by the same reference symbols are the same components as those in the second embodiment. Now, differences from the second embodiment are mainly described.

In FIGS. 11A, 11B and 11C, the wedge tapping device 10 includes the tapping portion 20 configured to tap the wedge 3 of the rotating electrical machine, the energy supplying portion 40 configured to apply the tapping energy to the tapping portion 20, the absorbing portion 50 configured to absorb the surplus energy generated when the tapping portion 20 taps the wedge 3, and the tapping arm 30, on which the tapping portion 20 is disposed, and which has a longitudinal direction in a direction perpendicular to the direction in which the tapping portion 20 performs tapping. In this case, the absorbing portion 50 suppresses the energy to be applied to the tapping portion 20.

Further, the tapping arm 30 has the longitudinal direction in a direction perpendicular to the direction in which the tapping portion 20 performs tapping. The tapping arm 30 is disposed so that its longitudinal direction is perpendicular to the circumferential direction of the rotor 6 when tapping is performed in the gap between the rotor 6 and the stator 4 of the rotating electrical machine. The tapping portion 20, the energy supplying portion 40, and the absorbing portion 50 are disposed in parallel along the longitudinal direction of the tapping arm 30. Further, the points at which the tapping arm 30 is in contact with the tapping portion 20, the energy supplying portion 40, and the absorbing portion 50 may be located on one straight line in the longitudinal direction of the tapping arm 30. In this case, less torsion force is applied to the tapping arm 30, and there is provided such an effect that the tapping arm 30 can be thinned.

Further, the wedge tapping device 10 includes the tapping portion 20 at the end of the tapping arm 30. Further, the wedge tapping device 10 includes the pivot support portion 33 disposed on the casing 11 of the wedge tapping device 10 and configured to support the tapping arm 30 so as to be pivotable. Further, the distance between the fulcrum of the pivot support portion 33 and the tapping portion 20 is larger than the distance between the fulcrum of the pivot support portion 33 and the energy supplying portion 40 and the distance between the fulcrum and the absorbing portion 50.

Further, the wedge tapping device 10 includes the cam 62 configured to cause the tapping arm 30 to pivot about the fulcrum of the pivot support portion 33, and the rotation driving portion (motor 61) configured to rotate the cam 62. In this case, the rotation axis of the rotation driving portion (motor 61) is oriented perpendicular to the pivot axis of the tapping arm 30.

In FIG. 11A, the cam 62 is a plate-shaped cam whose diameter gradually changes similarly to those illustrated in FIGS. 4A, 4B, 4C, 5A and 5B. In this case, similarly to the above, the cam 62 has a shape that enables the tapping arm 30 to rotate in accordance with the rotation of the rotation driving portion (motor 61), to thereby store energy in the energy supplying portion 40 (tapping elastic body 42) and primarily release the stored energy to rotate the tapping arm 30. Specifically, the cam 62 has such a diameter that a diameter of a part in contact with the tapping arm when the energy supplying portion 40 (tapping elastic body 42) releases the energy (right before the release) is larger than a diameter of a part in contact with the tapping arm when the energy supplying portion 40 (tapping elastic body 42) stores energy (at the time of start of storage). The cam 62 is configured to be movable in the direction of the rotation axis of the motor 61. Therefore, the cam 62 moves relatively to the rotation fulcrum of the pivot support portion 33. Further, when the cam 62 moves, the position at which the tapping arm 30 is brought into contact with the cam 62 changes. When the position of the cam 62 moves in a direction approaching the rotation fulcrum of the pivot support portion 33, the operation range of the tapping arm 30 increases, and when the position of the cam 62 moves in a direction separating from the fulcrum, the operation range of the tapping arm 30 decreases. When the operation range of the tapping arm 30 increases, larger energy is stored in a tapping arm driving portion 41 serving as the energy supplying portion 40, and the energy to be released is also increased to increase the tapping force. When the operation range of the tapping arm 30 increases, smaller energy is stored in the tapping arm driving portion 41. The energy to be released is also decreased to decrease the tapping force. The tapping arm driving portion 41 may be the tapping elastic body 42 instead.

Further, as in the following example (FIGS. 13A, 13B and 13C), the tapping arm 30 may be configured so that the position relative to the rotation fulcrum of the pivot support portion 33 changes in the longitudinal direction of the tapping arm 30. In this case, the position of the tapping portion 20 moves relatively to the rotation fulcrum of the pivot support portion 33. Unlike the above-mentioned case in which the cam 62 moves, the angle of the operation range of the tapping arm 30 does not change. When the position of the tapping portion 20 moves relatively to the rotation fulcrum of the pivot support portion 33, the tapping stroke of the tapping portion 20 changes.

When the tapping arm 30 and the tapping arm driving portion 41 are not fixed, the distance between the rotation fulcrum of the pivot support portion 33 and the tapping arm driving portion 41 does not change, and the energy stored in the tapping arm driving portion 41 serving as the energy supplying portion 40 does not change. The distance between the tapping portion 20 and the rotation fulcrum of the pivot support portion 33 changes, and hence the tapping stroke and the tapping force of the tapping portion 20 change. When the tapping arm 30 moves in a direction in which the distance between the tapping portion 20 and the rotation fulcrum of the pivot support portion 33 is reduced, the stroke of the tapping portion 20 is reduced and the tapping force is reduced.

FIG. 11(b) is an illustration of a state in which the rotary shaft of the motor 61 is rotated to store energy in the tapping arm driving portion 41 serving as the energy supplying portion 40. Further, FIG. 11(c) is an illustration of a state in which the rotary shaft of the motor 61 is rotated to release the energy from the tapping arm driving portion 41 serving as the energy supplying portion 40 so that the tapping portion 20 taps the wedge.

Figure 12A:
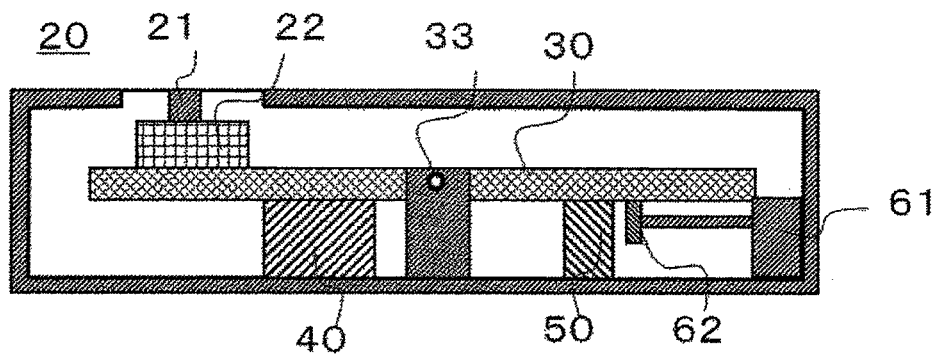
FIGS. 12A, 12B and 12C are sectional views for illustrating an operation at a time when a cam is moved in the wedge tapping device according to the third embodiment of the present invention.
Figure 12B:
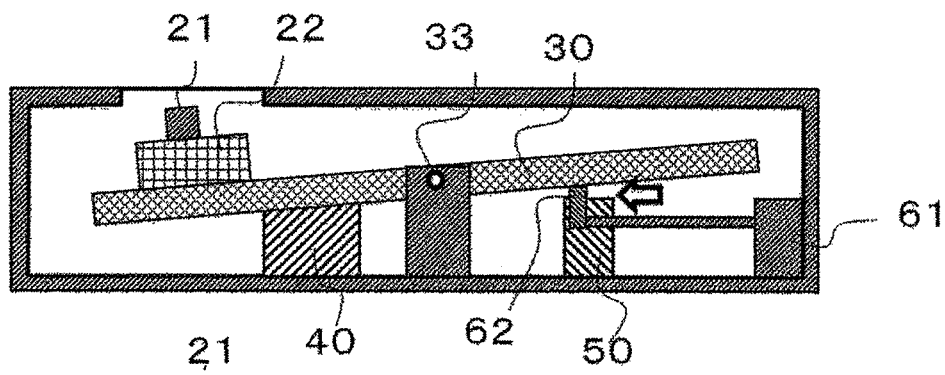
Figure 12C:
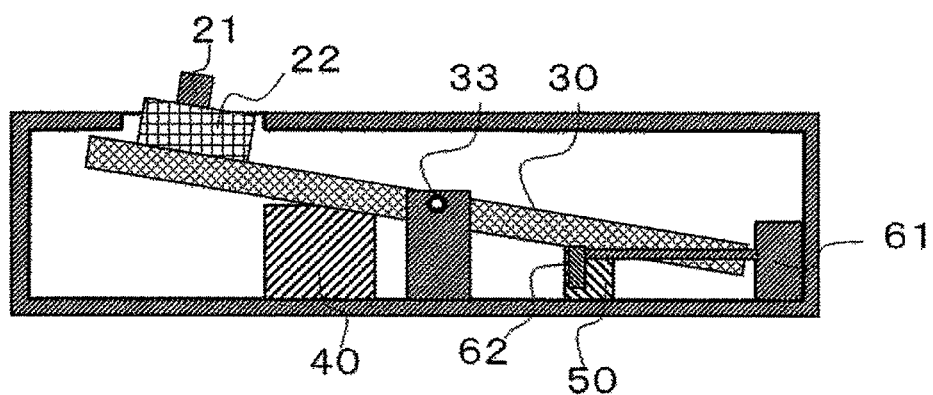

FIGS. 12A, 12B and 12C are illustrations of a state in which the cam 62 is moved in a direction of approaching the rotation fulcrum of the pivot support portion 33 from the position of the cam 62 illustrated in FIGS. 11A, 11B and 11C. Further, FIG. 12A is an illustration of a state in which no energy is stored in the tapping arm driving portion 41, FIG. 12B is an illustration of a state in which the tapping arm driving portion 41 stores energy, and FIG. 12C is an illustration of a state in which the energy in the tapping arm driving portion 41 is released.

Figure 13A:
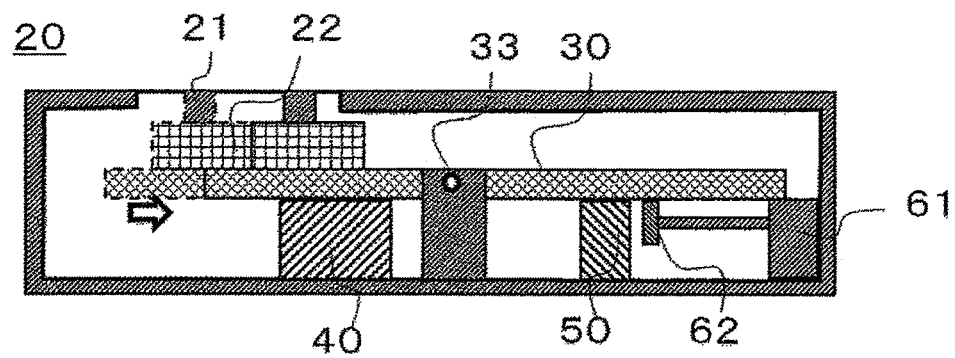
FIGS. 13A, 13B and 13C are sectional views for illustrating an operation at a time when a tapping arm is moved in the wedge tapping device according to the third embodiment of the present invention.
Figure 13B:
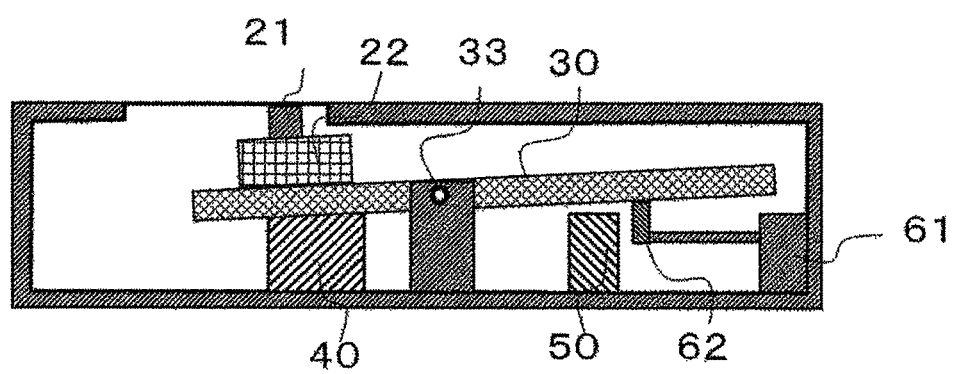
Figure 13C:
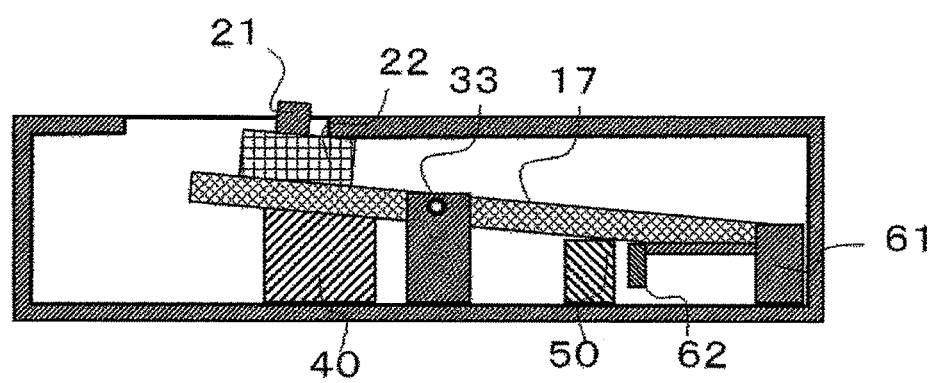

FIGS. 13A, 13B and 13C are illustrations of a state in which the tapping arm 30 of FIGS. 11A, 11B and 11C is moved in a direction in which the distance between the tapping portion 20 and the rotation fulcrum of the pivot support portion 33 is reduced in the longitudinal direction of the tapping arm 30. Further, FIG. 13A is an illustration of a state in which no energy is stored in the tapping arm driving portion 41, FIG. 13B is an illustration of a state in which the tapping arm driving portion 41 stores energy, and FIG. 13C is an illustration of a state in which the energy in the tapping arm driving portion 41 is released.

In the state of the cam 62 of FIG. 12B and FIG. 12C (state in which the cam 62 is close to the rotation fulcrum of the pivot support portion 33), the operation range (operation angle) of the tapping arm 30 is increased. Therefore, the energy stored in the tapping arm driving portion 41 is larger than that in the state of the cam 62 illustrated in FIGS. 11A, 11B and 11C, and the tapping force is also increased.

In FIGS. 13A, 13B and 13C, the tapping arm 30 is moved in a direction in which the distance between the tapping portion 20 and the rotation fulcrum of the pivot support portion 33 is reduced in the longitudinal direction of the tapping arm 30, and hence the tapping stroke of the tapping portion 20 is reduced, and the tapping force is also reduced.

In FIGS. 13A, 13B and 13C, the cam 62 is described as a simple plate cam. In FIGS. 13A, 13B and 13C, the angle in which the tapping arm 30 can be actuated does not change even when the tapping arm 30 is moved. Therefore, the cam 62 whose diameter changes in the rotation axis direction, which has been described in the second embodiment, can be used. With use of such a cam 62, the cam 62 and the tapping arm 30 are brought into linear contact with each other, and thus a large force can be exerted. Further, there is provided such an effect that, even when the tapping arm driving portion 41 capable of storing large energy is used, the cam 62 and the tapping arm 30 do not wear, and the tapping force can be maintained for a long period of time.

As described above, when the cam 62 is moved in the rotation axis direction of the motor 61, or when the distance between the tapping portion 20 and the rotation fulcrum of the pivot support portion 33 is changed, the tapping stroke and the tapping force of the tapping arm 30 can be changed. This configuration can be rephrased as follows. That is, the cam 62 and the tapping arm 30 are configured to be relatively movable, and when the relative position changes, the rotation range of the tapping arm 30 changes, and thus the energy released from the tapping arm driving portion 41 (energy supplying portion 40 or tapping elastic body 42) or the arrival range of the tapping portion 20 changes.

According to the third embodiment, when the cam 62 is moved in the rotation axis direction of the motor 61, or when the distance between the tapping portion 20 and the rotation fulcrum of the pivot support portion 33 is changed, the tapping stroke and the tapping force of the tapping arm 30 can be changed. Therefore, in wedge inspection of individual rotating electrical machines, the tapping stroke and the tapping force can be appropriately adjusted.

Further, the above-mentioned movement may be able to be performed manually or may be able to be adjusted remotely. When the movement can be adjusted remotely, in a case where the wedge is tapped and the tapping force is too large or too small or the stroke is too large or too small, the tapping force or the stroke can be adjusted to apply appropriate tapping. Further, the third embodiment is effective because the same wedge tapping device 10 can be used for adjustment of the tapping force and the stroke when the wedge is inspected in different rotating electrical machines and it is conceivable that the distance from the surface of the stator 4 to the wedge 3 varies.

Fourth Embodiment

Figure 14A:
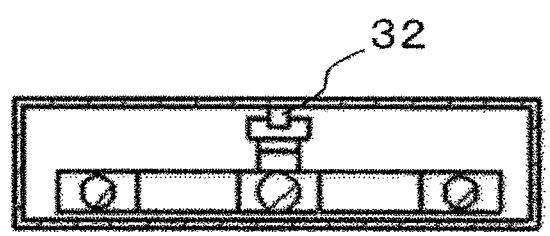
FIGS. 14A, 14B and 14C are views for illustrating a configuration of a wedge tapping device according to a fourth embodiment of the present invention.
Figure 14B:
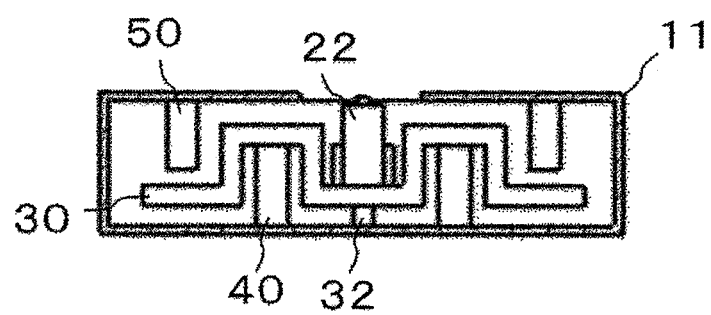
Figure 14C:
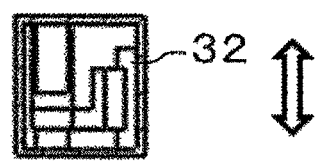

FIGS. 14A, 14B and 14C are configuration views for illustrating a wedge tapping device 10 for a rotating electrical machine according to a fourth embodiment of the present invention. The wedge tapping device 10 according to the fourth embodiment includes the tapping portion 20 configured to tap the wedge 3 of the rotating electrical machine, the energy supplying portion 40 configured to apply the tapping energy to the tapping portion 20, the absorbing portion 50 configured to absorb the surplus energy generated when the tapping portion 20 taps the wedge 3, and the tapping arm 30, on which the tapping portion 20 is disposed, and which has the longitudinal direction in the direction perpendicular to the direction in which the tapping portion 20 performs tapping. In this case, the absorbing portion 50 suppresses the energy to be applied to the tapping portion 20.

The fourth embodiment differs from the above-mentioned embodiments as that of FIGS. 4A, 4B and 4C in that the tapping arm 30 performs a translation operation without being supported by the pivot support portion 33.

In FIGS. 14A, 14B and 14C, a tapping plate 31 serving as the tapping arm 30 is mounted to the linear guide 32 configured to restrict the motion of the tapping arm 30 to translation so that the tapping plate 31 is linearly movable in a direction in which the tapping force measuring instrument 22 included in the tapping portion 20 can measure the force.

Further, the energy supplying portion 40 serving as tapping plate driving means is mounted so as to enable drive in the linear movement direction. That is, the driving direction of the energy supplying portion 40 serving as the tapping plate driving means is the same as the tapping direction, and is perpendicular to the tapping arm 30. Further, two energy supplying portions 40 may be disposed in the longitudinal direction of the tapping arm 30. In this case, the tapping portion 20 may be disposed between the two energy supplying portions 40. The energy supplying portion 40 serving as the tapping plate driving means can be constructed of, for example, a voice coil motor, a solenoid coil, or a piezoelectric actuator. The energy supplying portion 40 may be the tapping elastic body 42 instead.

The double-tapping preventing elastic body 51 serving as the absorbing portion 50 is mounted on the casing 11 side in which the wedge tapping device 10 is mounted. Now, the setting of the double-tapping preventing elastic body 51 is described. Unless the tapping plate 31 approaches the double-tapping preventing elastic body 51 to the extent that the tapping plate 31 can tap the wedge 3, the double-tapping preventing elastic body 51 is not brought into contact with the tapping plate 31. Therefore, the double-tapping preventing elastic body 51 is structured so that the double-tapping preventing elastic body 51 cannot apply a force to the tapping plate 31 unless the tapping plate 31 approaches the double-tapping preventing elastic body 51 to the extent that the tapping plate 31 can tap the wedge 3.

Next, the operation at the time of tapping of the wedge is described. When the energy supplying portion 40 serving as the tapping plate driving means applies a force of pushing out the tapping plate 31 toward the wedge 3, the tapping portion 20 (including the tapping force measuring instrument 22) taps the wedge 3.

At this time, the tapping plate 31 contracts the double-tapping preventing elastic body 51. Therefore, the double-tapping preventing elastic body 51 applies a force to the tapping plate 31 in a direction of returning the tapping plate 31 to its original position. In this manner, the tapping portion 20 (tapping force measuring instrument 22) is separated from the wedge 3 without tapping the wedge 3 twice. After that, the energy supplying portion 40 serving as the tapping plate driving means returns the tapping plate 31 to its original position. The energy supplying portion 40 serving as the tapping plate driving means pushes out the tapping plate 31 again, and thus the above-mentioned operation is repeated.

In the wedge tapping device 10 according to the fourth embodiment, the energy supplying portion 40 serving as the tapping plate driving means is constructed of, for example, a voice coil motor, a solenoid coil, or a piezoelectric actuator. Therefore, the energy supplying portion 40 serving as the tapping plate driving means can turn on or off the current to enable driving or canceling of the drive. With use of a controller configured to control the current, the tapping timing of the tapping portion 20 can be controlled. Further, adjustment of the supply current enables the tapping stroke, the tapping force, or both of the tapping stroke and the tapping force to be changed.

According to the wedge tapping device 10 for a rotating electrical machine of the fourth embodiment, the tapping portion 20, the energy supplying portion 40 serving as the tapping plate driving means, and a constituent element related to the tapping of the double-tapping preventing elastic body 51 are disposed in parallel in a direction orthogonal to the thickness direction of the device. Further, the movement direction of the tapping portion 20, the driving direction of the energy supplying portion 40 serving as the tapping plate driving means, and the displacement direction of the double-tapping preventing elastic body 51 are all set to the tapping direction. In this manner, there is provided such an effect that the thickness of the device can be reduced.

Further, although the accuracy of determining looseness of the wedge 3 is reduced unless the wedge 3 is tapped with a sufficiently strong force, when the configuration of the fourth embodiment is adopted, the thickness of the wedge tapping device 10 for a rotating electrical machine can be reduced, and the device to be used for the tapping arm driving portion 41 serving as the energy supplying portion 40 can be relaxed in dimensional limitation. Thus, there is provided such an effect that a stronger device can be constructed.

Fifth Embodiment

Figure 15:
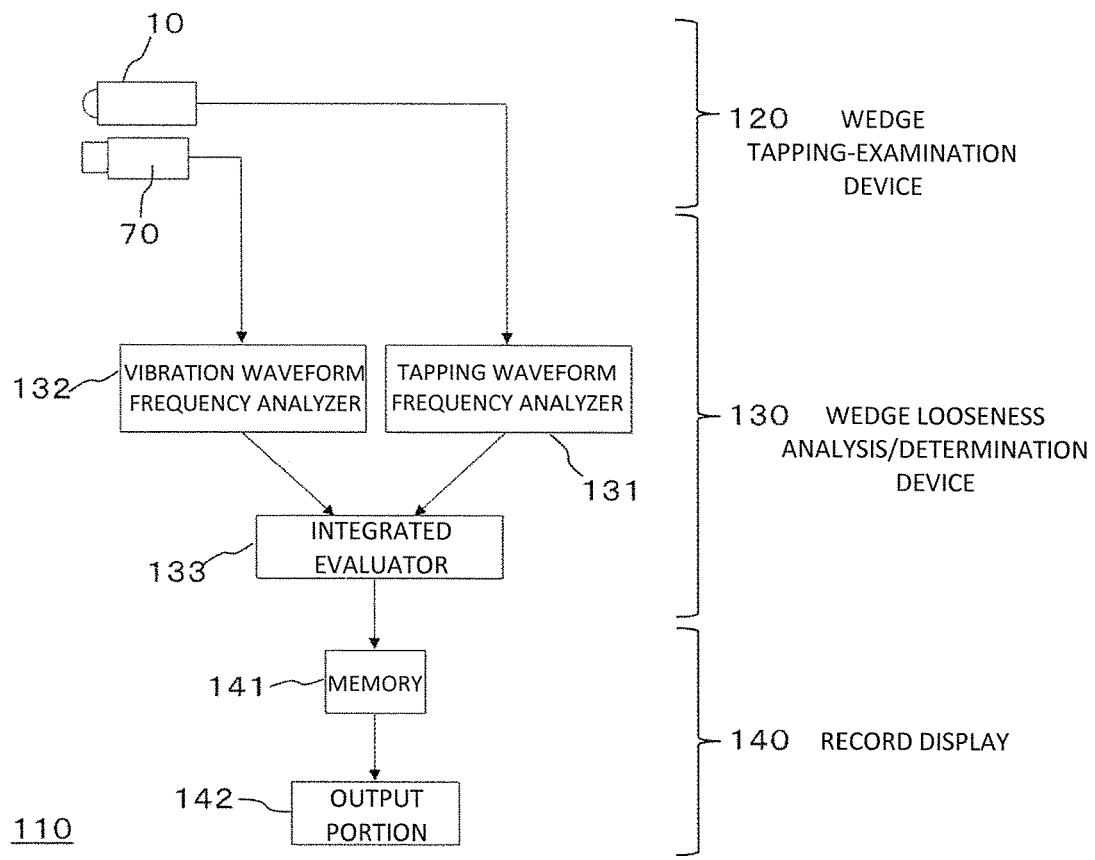
FIG. 15 is a block diagram for illustrating a wedge inspection system for a rotating electrical machine according to a fifth embodiment of the present invention.

FIG. 15 is a block diagram for illustrating a wedge looseness determination system for a rotating electrical machine, which uses the wedge tapping device 10 of any one of the above-mentioned embodiments. A wedge inspection system 110 according to a fifth embodiment of the present invention includes a wedge tapping-examination device 120, a wedge looseness analysis/determination device 130, and a record display 140. In this case, the wedge tapping device 10 includes the tapping portion 20, the tapping arm 30, the energy supplying portion 40, and the absorbing portion 50 in any one of the above-mentioned embodiments. The wedge tapping device 10 may further include the above-mentioned cam 62 and rotation driving portion (motor 61).

The wedge tapping-examination device 120 includes the wedge tapping device 10, which includes the tapping force measuring instrument 22 configured to detect a tapping force waveform obtained when the wedge tapping device 10 taps the wedge 3, and is configured to tap the wedge 3, and a wedge vibration detection device 70 configured to detect a vibration of the wedge 3 obtained when the wedge tapping device 10 taps the wedge 3.

The wedge looseness analysis/determination device 130 includes a tapping waveform frequency analyzer 131 and a vibration waveform frequency analyzer 132 configured to analyze the frequency characteristic of the tapping force waveform and the frequency characteristic of the wedge vibration waveform, respectively, which are obtained by the wedge tapping-examination device 120, and an integrated evaluator 133 configured to integrate the respective frequency characteristics of the analysis results, and then compare and evaluate the result with a determination reference set in advance to quantify the determination result.

The record display 140 includes a memory 141 configured to store and record the data, and an output portion 142 configured to display the result.

First, the wedge tapping-examination device 120 subjects the wedge 3 to tapping, and transmits the tapping force information and the wedge vibration information to the wedge looseness analysis/determination device 130. The tapping force information refers to a tapping force waveform measured by the tapping force measuring instrument 22. The wedge vibration information refers to a wedge vibration waveform measured by the wedge vibration detection device 70.

Next, in the wedge looseness analysis/determination device 130, the tapping waveform frequency analyzer 131 receives the tapping force information, and analyzes the frequency component to obtain the frequency characteristic of the tapping force. Further, the vibration waveform frequency analyzer 132 receives the wedge vibration information, and analyzes the frequency component to obtain the frequency characteristic of the wedge vibration. The integrated evaluator 133 obtains a frequency characteristic of a tapping-examination model from the input of tapping to the wedge 3 to the vibration output based on the tapping force frequency characteristic and the wedge vibration frequency characteristic, which are obtained by the tapping waveform frequency analyzer 131 and the vibration waveform frequency analyzer 132, respectively. In this case, the determination reference set in advance and the frequency of the appearing peak are compared and evaluated.

The record display 140 receives the comparison evaluation result obtained by the wedge looseness analysis/determination device 130 to store the result in the memory 141. At this time, the number of slots and the number of wedges in each slot differ depending on the type of the rotating electrical machine, and hence those numbers are input in advance. Further, it is desired to automatically record the corresponding slot and the wedge number simultaneously in synchronization with each evaluation result. The output portion 142 refers to the result recorded in the memory 141 to display the result on a screen.

Figure 16:
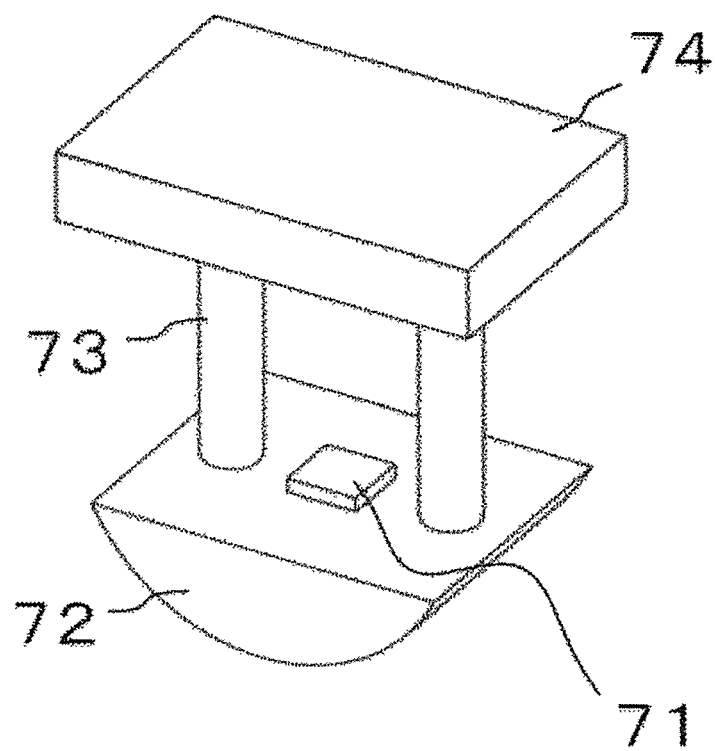
FIG. 16 is a view for illustrating a configuration of a wedge vibration detection device in the fifth embodiment of the present invention.

FIG. 16 is a configuration view for illustrating the wedge vibration detection device 70 of FIG. 15. A contact tool 72 having a vibration measuring portion 71 mounted thereon is mounted to a vibration measuring support portion 74 through intermediation of a vibration measuring elastic body 73. When the contact tool 72 is brought into contact with the wedge 3 under a state in which the vibration measuring elastic body 73 is contracted, the contact tool 72 is pressed against the wedge 3, and the vibration of the wedge 3 is transmitted to the vibration measuring portion 71 through intermediation of the contact tool 72.

What measures the vibration of the wedge 3 is not limited to a contact-type vibration sensor or acceleration sensor, and it is only required to detect the vibration of the wedge 3. For example, there may be given a sound collecting microphone or a displacement sensor. When the vibration of the wedge 3 is detected in a non-contact manner, such a configuration as that of FIG. 16 is not required, and the vibration measuring portion 71 is only required to be disposed in the vicinity of the wedge tapping device 10 or in the vicinity of the wedge 3. The vibration measuring portion 71 can also be regarded as a part of the wedge tapping device 10. Further, the wedge tapping-examination device 120 may be constructed by including the vibration measuring portion 71 and the wedge tapping device 10.

Figure 17A:
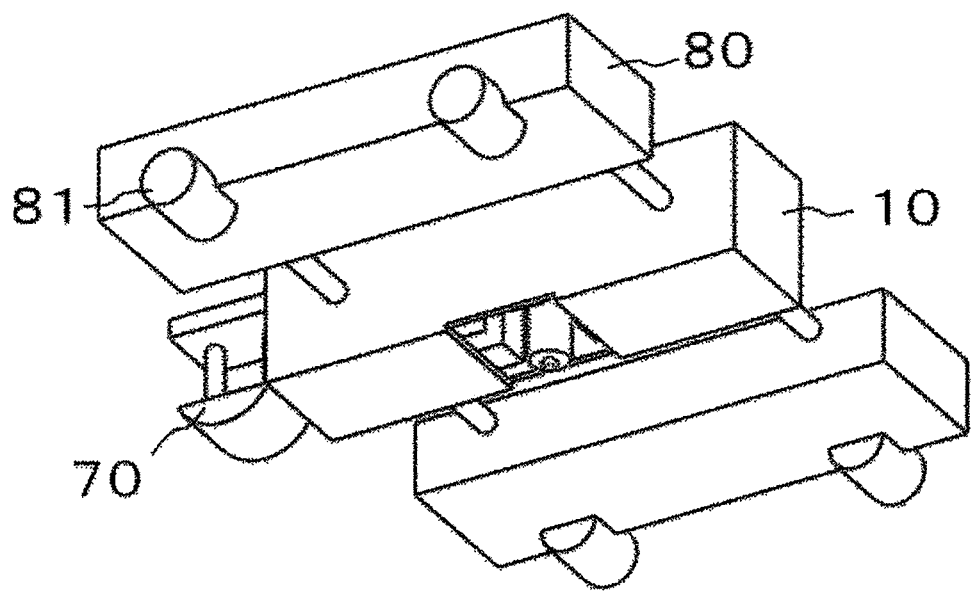
FIGS. 17A and 17B are views for illustrating a configuration in which the wedge tapping device, the wedge vibration detection device, and a drive device are combined in the fifth embodiment of the present invention.
Figure 17B:
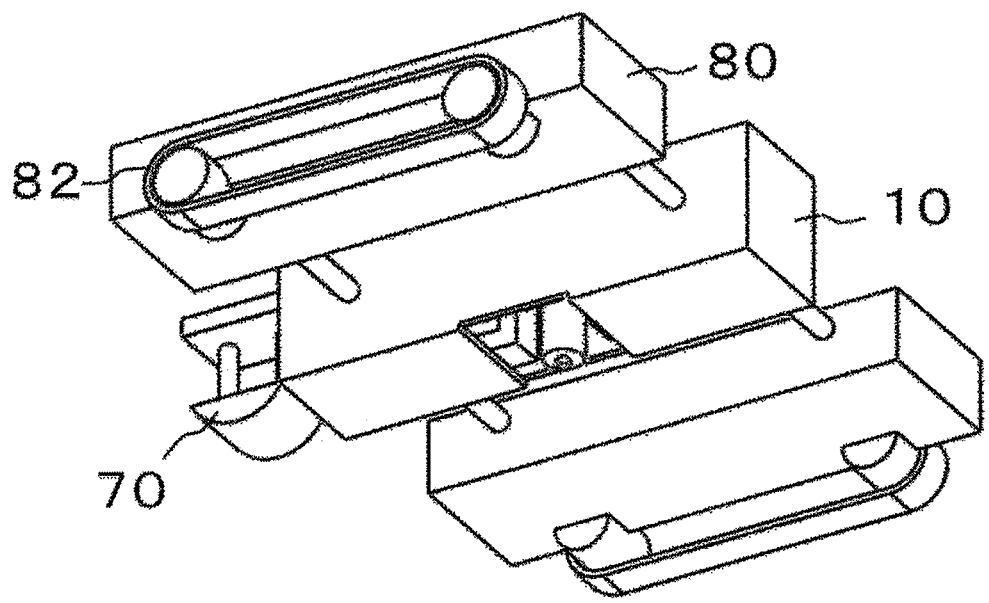

FIGS. 17A and 17B are illustrations of an example of a configuration for applying the wedge inspection system 110 for a rotating electrical machine according to the fifth embodiment of the present invention to a rotating electrical machine. The wedge inspection system 110 for a rotating electrical machine includes the wedge tapping device 10 of any one of the above-mentioned embodiments, the wedge vibration detection device 70, and a driving portion 80. The wedge inspection system 110 for a rotating electrical machine further includes a signal processor including the wedge looseness analysis/determination device 130 and the record display 140.

The driving portion 80 has a traveling function for scanning the gap between the rotor 6 and the stator 4 of the rotating electrical machine. The driving portion 80 is further required to have an adsorption function for sufficiently pressing the wedge tapping device 10 or the wedge tapping device 10 and the vibration measuring portion 71 against the wedge 3 when the wedge is tapped, and also for withstanding the reaction force when the wedge is tapped. Examples of the former function include a wheel 81 and a crawler 82, and examples of the latter function include magnets and air suction. The wedge tapping device 10 and the wedge vibration detection device 70 are mounted to the driving portion 80 and enter the rotating electrical machine by the driving portion 80. In this manner, the wedge looseness inspection can be performed at any position. Further, the wedge tapping-examination device 120 may be constructed by including those wedge tapping device 10 and wedge vibration detection device 70 mounted to the driving portion 80.

Further, in order to inspect the stator 4 of the rotating electrical machine over its entire periphery, the driving portion 80 presses the wedge tapping device 10 or the wedge tapping device 10 and the vibration measuring portion 71 against the wedge 3. In this manner, the wedge tapping device 10 or the wedge tapping device 10 and the vibration measuring portion 71 may stand upright or inversed so as to enable tapping in a horizontal direction or in a vertically upward direction of the rotating electrical machine to measure the vibration.

According to the wedge inspection system 110 of the fifth embodiment of the present invention, the constituent elements related to tapping are disposed in parallel in the direction orthogonal to the thickness direction of the device. Thus, the device including the measuring instrument configured to detect the tapping input waveform can be thinned. In this manner, in the wedge looseness inspection, without pulling out the rotor 6 of the rotating electrical machine, the operation from the tapping input at the time of tapping the wedge to the wedge vibration is collectively treated as one tapping-examination model. A method of analyzing the frequency characteristic in the tapping-examination model can be adopted. Thus, influences of the change in tapping magnitude and frequency characteristic with respect to the change in situation and environment can be taken into consideration, and hence robust looseness evaluation can be achieved.

Further, with a sufficient strength of tapping force being ensured, while the looseness determination accuracy and the reliability are enhanced, the inspection is possible by inserting the device through the gap between the rotor 6 and the stator 4 of the rotating electrical machine. In this manner, a process involving pulling out the rotor of the rotating electrical machine and re-inserting and adjusting the rotor can be eliminated, and thus the inspection work period can be greatly reduced.

REFERENCE SIGNS LIST 1 coil, 2 ripple spring, 3 wedge, 4 stator, 5 shim, 6 rotor, 10 wedge tapping device, 11 casing, 20 tapping portion, 21 tapping member, 22 tapping force measuring instrument, 30 tapping arm, 31 tapping plate, 32 linear guide, 33 pivot support portion, 40 energy supplying portion, 41 tapping arm driving portion, 42 tapping elastic body, 50 absorbing portion, 51 double-tapping preventing elastic body, 61 motor, 62 cam, 70 wedge vibration detection device, 71 vibration measuring portion, 72 contact tool, 73 vibration measuring elastic body, 74 vibration measuring support portion, 80 driving portion, 81 wheel, 82 crawler, 110 wedge inspection system, 120 wedge tapping-examination device, 130 wedge looseness analysis/determination device, 131 tapping waveform frequency analyzer, 132 vibration waveform frequency analyzer, 133 integrated evaluator, 140 record display, 141 memory, 142 output portion

The invention claimed is:

1. A wedge tapping device for a rotating electrical machine, which is to be inserted through a gap between a rotor and a stator of the rotating electrical machine to tap a wedge of the rotating electrical machine, the wedge tapping device comprising:
   a tapping portion, which is configured to tap the wedge of the rotating electrical machine, and includes a tapping force measuring instrument configured to measure a tapping force of the tapping;
   an energy supplying portion configured to apply tapping energy to the tapping portion;
   a tapping arm, on which the tapping portion is disposed, and which has a longitudinal direction in a direction perpendicular to a direction in which the tapping portion performs tapping;
   a cam brought into contact with the tapping arm;
   a rotation driving portion configured to rotate the cam; and
   an absorbing portion configured to suppress energy to be applied to the tapping portion,
   wherein the rotation driving portion has a rotation axis oriented perpendicular to a tapping direction of the tapping portion,
   wherein the tapping arm is supported so as to be rotatable about a fulcrum fixed to a main body,
   wherein the cam has a shape that enables the energy supplying portion to store the energy and release the stored energy at once in accordance with rotation of the rotation driving portion, and
   wherein a distance between the fulcrum and the tapping portion is larger than a distance between the fulcrum and the energy supplying portion and a distance between the fulcrum and the absorbing portion.

2. A wedge tapping device for a rotating electrical machine according to claim 1, further comprising a vibration measuring portion configured to measure a vibration waveform of the wedge at a time when the tapping portion taps the wedge.

3. A wedge inspection system for a rotating electrical machine, comprising the wedge tapping device for a rotating electrical machine of claim 2,
   the wedge inspection system being configured to inspect the wedge with use of the vibration waveform and a tapping input waveform obtained by the tapping force measuring instrument of the wedge tapping device for a rotating electrical machine.

4. A wedge tapping device for a rotating electrical machine, which is to be inserted through a gap between a rotor and a stator of the rotating electrical machine to tap a wedge of the rotating electrical machine, the wedge tapping device comprising:
   a tapping portion, which is configured to tap the wedge of the rotating electrical machine, and includes a tapping force measuring instrument configured to measure a tapping force of the tapping;
   an energy supplying portion configured to apply tapping energy to the tapping portion;
   a tapping arm, on which the tapping portion is disposed, and which has a longitudinal direction in a direction perpendicular to a direction in which the tapping portion performs tapping;
   a cam brought into contact with the tapping arm; and
   a rotation driving portion configured to rotate the cam,
   wherein the energy supplying portion includes a tapping elastic body configured to generate energy for rotating the tapping arm so that the tapping portion taps the wedge,
   wherein the rotation driving portion has a rotation axis oriented perpendicular to a tapping direction of the tapping portion,
   wherein the tapping arm is supported so as to be rotatable about a fulcrum fixed to a main body,
   wherein the cam has a shape that enables the energy supplying portion to store the energy and release the stored energy at once in accordance with rotation of the rotation driving portion, and
   wherein the cam has a diameter that is larger in a part in contact with the tapping arm right before the tapping elastic body releases the energy than in a part in contact with the tapping arm when the tapping elastic body starts storing the energy.

5. A wedge tapping device for a rotating electrical machine according to claim 4,
   wherein the cam has a diameter that changes in a circumferential direction in which the rotation driving portion rotates and in a rotation axis direction of the rotation driving portion, and
   wherein the tapping arm and the cam are brought into linear contact with each other.

6. A wedge tapping device for a rotating electrical machine according to claim 5, wherein an amount of change in diameter of the cam on a side farther from the fulcrum is larger than an amount of change in diameter of the cam on a side closer to the fulcrum.

7. A wedge tapping device for a rotating electrical machine according to claim 4,
   wherein the cam and the tapping arm are configured to be relatively movable, and
   wherein, when a relative position between the cam and the tapping arm changes, a rotation range of the tapping arm changes to change the energy released by the tapping elastic body or an arrival range of the tapping portion.

8. A wedge tapping method for a rotating electrical machine, which uses a wedge tapping device for a rotating electrical machine including:
   a tapping portion, which is configured to tap a wedge of the rotating electrical machine, and includes a tapping force measuring instrument configured to measure a tapping force of the tapping;

an energy supplying portion configured to apply tapping energy to the tapping portion;

a tapping arm, on which the tapping portion is disposed, and which has a longitudinal direction in a direction perpendicular to a direction in which the tapping portion performs tapping;

a cam brought into contact with the tapping arm; and a rotation driving portion configured to rotate the cam, the wedge tapping device being to be inserted through a gap between a rotor and a stator of the rotating electrical machine to tap the wedge of the rotating electrical machine, the energy supplying portion including a tapping elastic body configured to generate energy for rotating the tapping arm so that the tapping portion taps the wedge, the rotation driving portion having a rotation axis oriented perpendicular to a tapping direction of the tapping portion, the tapping arm being supported so as to be rotatable about a fulcrum fixed to a main body, the wedge tapping method comprising:

rotating the rotation driving portion to cause the cam to rotate the tapping arm, to thereby store the energy in the tapping elastic body; and rotating the rotation driving portion to cause the cam to rotate the tapping arm, to thereby release the energy stored in the tapping elastic body at once to rotate the tapping arm so that the tapping portion taps the wedge of the rotating electrical machine.

\* \* \* \* \*